United States Patent

Barbier et al.

[11] Patent Number: 5,994,569
[45] Date of Patent: Nov. 30, 1999

[54] DIHOMO-SECO-CHOLESTANES

[75] Inventors: Pierre Barbier, Rixheim, France; Peter Mohr, Basel, Switzerland; Marc Muller, Saint-Louis, France; Christopher Self, West Caldwell, N.J.

[73] Assignee: Hoffmann-La Roche Inc., Nutley, N.J.

[21] Appl. No.: 09/115,188

[22] Filed: Jul. 14, 1998

[30] Foreign Application Priority Data

Jul. 17, 1997 [EP] European Pat. Off. .............. 97112225

[51] Int. Cl.⁶ .................................................. C07C 401/00
[52] U.S. Cl. ............................................................ 552/653
[58] Field of Search ............................................. 552/653

[56] References Cited

U.S. PATENT DOCUMENTS

| | | | |
|---|---|---|---|
| 5,190,935 | 3/1993 | Binderup et al. | 514/167 |
| 5,447,924 | 9/1995 | Bretting | 514/167 |
| 5,532,228 | 7/1996 | Neef et al. | |
| 5,716,945 | 2/1998 | Grue-Sorensen | 514/167 |

FOREIGN PATENT DOCUMENTS

| | | |
|---|---|---|
| 0 441 467 | 8/1991 | European Pat. Off. . |
| 0 742 203 | 11/1996 | European Pat. Off. . |
| 0 771 789 | 5/1997 | European Pat. Off. . |
| WO 98/18754 | 5/1998 | WIPO . |

OTHER PUBLICATIONS

Tetrahedron Letters 1992: 2455 and 4365–4368, and 1996: 5589.
J.A.C.S. 119, 1997, 4353.
J. Clin. Invest. 93: 1733–1739 (1994).
Steroids, 1995, 60(4) pp. 324–332.
Steroids, 1997, 62(7), pp. 546–553.
Steroids, vol. 62 Nr. 7, 546–553 Aug. 1997—"E:mail message establishing the true publication date of Steroids, vol. 62, Nr. 7, pp. 546–553 as Aug. 7, 1997".

Primary Examiner—Jose' G. Dees
Assistant Examiner—Barbara Badio
Attorney, Agent, or Firm—George W. Johnston; Patricia S. Rocha-Tramaloni; Robert A. Silverman

[57] ABSTRACT

Polyunsaturated 24a,24b-dihomo-9,10-secocholestane derivatives of formula

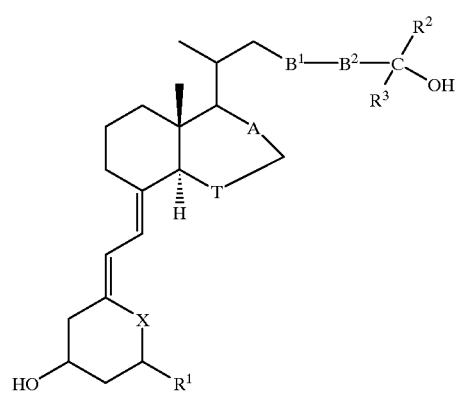

wherein A is a single or double bond,
$B^1$ and $B^2$ are each independently CH=CH or C≡C,
T is $CH_2$ or $CH_2CH_2$,
X is —$CH_2$— or >C=$CH_2$,
$R^1$ is H, F or OH,
$R^2$ and $R^3$ are each independently lower alkyl or $CF_3$, or $C(R^2,R^3)$ is $C_{3-6}$-cycloalkyl, are useful in the treatment or prevention of vitamin D dependent disorders and of IL-12-dependent autoimmune diseases, particularly psoriasis, basal cell carcinomas, disorders of keratinization and keratosis, leukemia, osteoporosis, hyperparathyroidism accompanying renal failure, multiple sclerosis, transplant rejection, graft vs. host disease, rheumatoid arthritis, insulin-dependent diabetes mellitus, inflammatory bowel disease, septic shock and allergic encephalomyelitis.

28 Claims, No Drawings

DIHOMO-SECO-CHOLESTANES

SUMMARY OF THE INVENTION

The invention relates to polyunsaturated 24a,24b-dihomo-9,10-seco-cholestane derivatives of formula I:

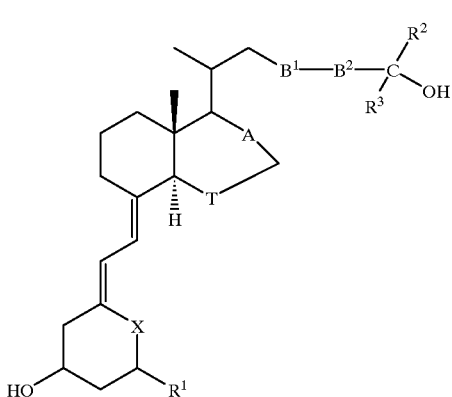

wherein
A is a single or double bond,
$B^1$ and $B^2$ are each independently CH=CH or C≡C,
T is $CH_2$ or $CH_2CH_2$,
X is —$CH_2$— or >C=$CH_2$,
$R^1$ is H, F or OH,
$R^2$ and $R^3$ are each independently $C_{1-4}$-alkyl or $CF_3$, or $C(R^2,R^3)$ is $C_{3-6}$-cycloalkyl.

The present invention furthermore relates to a process for the preparation of the compounds of formula I, pharmaceutical compositions containing the compounds of formula I, and the use of the compounds of formula I for the treatment of vitamin D dependent disorders and for the manufacture of pharmaceutical compositions for the treatment of vitamin D dependent disorders.

The term "vitamin D dependent disorders" refers to disorders which can be treated or prevented by the administration of compounds having vitamin D activity, such as vitamin $D_3$ or derivatives, in particular hydroxylated derivatives thereof, e.g. calcitriol or calcipotriol. Examples of such disorders are hyperproliferative skin diseases such as psoriasis, basal cell carcinomas, disorders of keratinization and keratosis; neoplastic diseases such as leukemia; disorders of the sebaceous glands such as acne and seborrhoic dermatitis; osteoporosis; hyperparathyroidism accompanying renal failure; and diseases which require modulation of the immune system, such as multiple sclerosis, transplant rejection and graft vs. host disease.

In particular, the compounds of formula I are useful in the prevention and treatment of IL-12-dependent autoimmune diseases such as rheumatoid arthritis, psoriasis, insulin-dependent diabetes mellitus, multiple sclerosis, inflammatory bowel disease, septic shock and allergic encephalomyelitis.

Another aspect of the invention are the intermediates of formulas II, IV, V and VI.

DETAILED DESCRIPTION OF THE INVENTION

As used herein $C_{1-4}$-alkyl denotes a straight or branched chain alkyl group containing 1 to 4 carbon atoms. Preferred $C_{1-4}$-alkyl groups are straight-chain alkyl groups, such as butyl, propyl ethyl, and particularly methyl. Preferred $C_{3-6}$-cycloalkyl groups are cyclobutyl, cyclopentyl and cyclohexyl.

In the formulas presented herein, the various substituents are illustrated as joined to the nucleus by one of the following notations: a wedged solid line indicates a substituent which is above the plane of the molecule and a wedged dotted line indicates a substituent which is below the plane of the molecule.

Preferred compounds of formula I are those wherein $B^1$ and $B^2$ are both —CH=CH—. More preferred are compounds of formula I in which the side chain is:

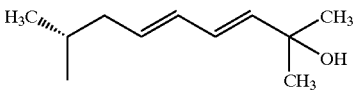

particularly:
(5Z,7E,23E,24aE)-(1R,3S)-24a,24b-dihomo-9,10-seco-cholesta-5,7,10(19),23,24a-pentaene-1,3,25-triol, and the following:
(7E,23E,24aE)-(1R,3R)-24a,24b-dihomo-19-nor-9,10-seco-cholesta-5,7,23,24a-tetraene-1,3,25-triol,
(5Z,7E,23E,24aE)-(1S,3S)-24a,24b-dihomo-9,10-seco-cholesta-5,7,10(19),23,24a-pentaene-1,3,25-triol,
(5Z,7E,23E,24aE)-(1S,3R)-17a,24a,24b-trihomo-9,10-seco-cholesta-5,7,10(19),23,24a-pentaene-1,3,25-triol,
(7E,23E,24aE)-(1R,3R)-17a,24a,24b-trihomo-19-nor-9,10-seco-cholesta-5,7,23,24a-tetraene-1,3,25-triol,
(5Z,7E,23E,24aE)-(3S)-17a,24a,24b-trihomo-9,10-seco-cholesta-5,7,10(19),23,24a-pentaene-3,25-diol,
(7E,23E,24aE)-(1R,3R)-17a,24a,24b-trihomo-19-nor-9,10-seco-cholesta-5,7,17,23,24a-pentaene-1,3,25-triol,
(5Z,7E,23E,24aE)-(1S,3R)-17a,24a,24b-trihomo-9,10-seco-cholesta-5,7,10(19),17,23,24a-hexaene-1,3,25-triol,
(5Z,7E,23E,24aE)-(1S,3S)-17a,24a,24b-trihomo-9,10-seco-cholesta-5,7,10(19),17,23,24a-hexaene-1,3,25-triol,
(5Z,7E,23E,24aE)-(1S,3S)-17a,24a,24b-trihomo-9,10-seco-cholesta-5,7,10(19),23,24a-pentaene-1,3,25-triol,
(7E,23E,24aE)-(1R,3R)-24a,24b-Dihomo-19-nor-9,10-seco-cholesta-5,7,16,23,24a-pentaene-1,3,25-triol,
(5Z,7E,23E,24aE)-(1S,3R)-24a,24b-Dihomo-9,10-seco-cholesta-5,7,10(19),16,23,24a-hexaene-1,3,25-triol, and
(5Z,7E,23E,24aE)-(3S)-24a,24b-Dihomo-9,10-seco-cholesta-5,7,10(19),16,23,24a-hexaene-3,25-diol.

Further preferred compounds of formula I are those wherein $B^1$ is —CH=CH— and $B^2$ is —C≡C—; that is, compounds of formula I in which the side-chain is

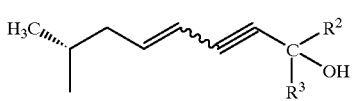

particularly
(7E,23E)-(1R,3R)-17a,24a,24b-Trihomo-19-nor-9,10-seco-cholesta-5,7,23-triene-24a-yne-1,3,25-triol,
(5Z,7E,23E)-(1S,3R)-17a,24a,24b-Trihomo-9,10-seco-cholesta-5,7,10(19),23-tetraene-24a-yne-1,3,25-triol,
(7E,23E)- and (7E,23Z)-(1R,3R)-24a,24b-dihomo-19-nor-9,10-seco-cholesta-5,7,23-trien-24a-yne-1,3,25-triol,
(7E,23E)- and (7E,23Z)-(1R,3R)-24a,24b,26a,26b-tetrahomo-19-nor-9,10-seco-cholesta-5,7,23-trien-24a-yne-1,3,25-triol,
(7E,23E)- and (7E,23Z)-(1R,3R)-26,26,26,27,27,27-hexyfluoro-24a,24b-dihomo-19-nor-9,10-seco-cholesta-5,7,23-trien-24a-yne-1,3,25-triol, (7E,23E,24aE)- and (7E,23Z,24aE)-(1R,3R)-24a,24b,26a,26b-tetrahomo-19-nor-9,10-seco-cholesta-5,7,23,24a-tetraen-24a-yne-1,3,25-triol, and (7E,23E,24aE)- and (7E,23Z,24aE)-(1R,3R)-26,26,26,27,27,27-hexafluoro-24a,24b-dihomo-19-nor-9,10-seco-cholesta-5,7,23,24a-tetraen-24a-yne-1,3,25-triol.

A further group of preferred compounds are those wherein $B^1$ is —CH═CH—, $B^2$ is —C≡C— and $C(R^2, R^3)$ is $C_{3-6}$-cycloalkyl, in particular (7E,23E)- and (7E,23Z)-(1R,3R)-25-(1-hydroxy-cyclopentyl)-24a,24b-dihomo-19-nor-9,10-seco-cholesta-5,7,23-trien-24a-yne-1,3-diol, (7E,23E,24aE)- and (7E,23Z,24aE)-(1R,3R)-25-(1-hydroxycyclopentyl)-24a,24b-dihomo-19-nor-9,10-seco-cholesta-5,7,23,24a-tetraen-24a-yne-1,3-diol, The compounds of formula I can be obtained by cleavage of any silyl-protecting group L and L' contained in a compound of formula II

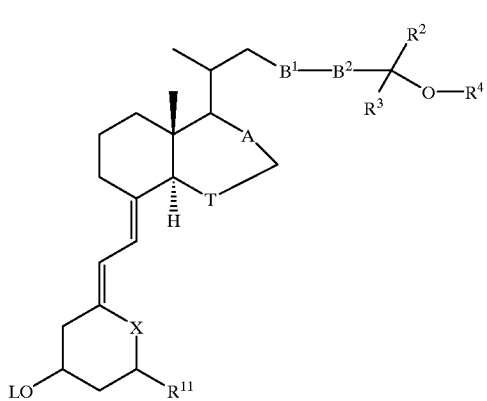

II wherein $R^{11}$ is H, F or O—L, and $R^4$ is H or L', and A, $B^1$, $B^2$, T, R, $R^2$ and $R^3$ are as defined earlier.

Examples of silylprotecting groups L and L' are tert-butyl-dimethylsilyl (TBDMS), tert-butyl-diphenylsilyl (TBDPS) or trimethylsilyl (TMS).

The cleavage of silyl-protecting groups in the compounds II can be effected by tetrabutylammonium fluoride (TBAF) in a solvent such as tetrahydrofuran (THF) at a temperature up to 60° C.

The compounds of formula II wherein both $B^1$ and $B^2$ are CH═CH, are obtained by coupling a phosphinoxide of formula III

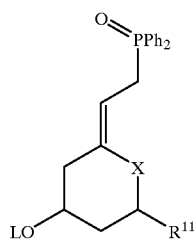

III with a ketone of formula IV

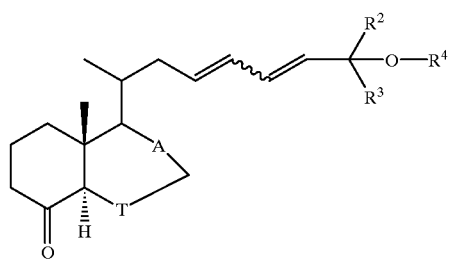

IV

The coupling can be effected by reacting a solution of the phosphinoxide III in THF with butyl lithium and then with a ketone IV at −78° C.

The ketones IV can be obtained by oxidation of the corresponding diols of formula V

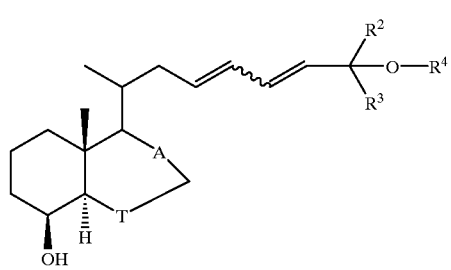

V if desired followed by silylation of the obtained hydroxy ketones of formula

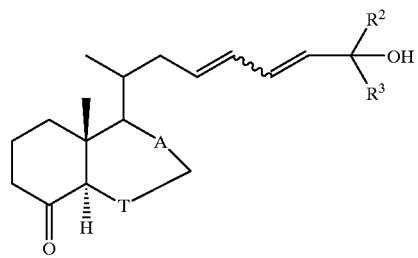

VI

The oxidation can be effected in N,N-dimethylformide (DMF) or in $CH_2Cl_2$ with pyridinium dichromate (PDC), or with 4-methylmorpholine N-oxide and catalytic amounts of tetrapropylammonium perrhutenate, in the presence of molecular sieve.

The silylation of VI can be effected in THF or in $CH_2Cl_2$ e.g. with TMS-imidazole.

The diols V can be obtained from esters of formula VII

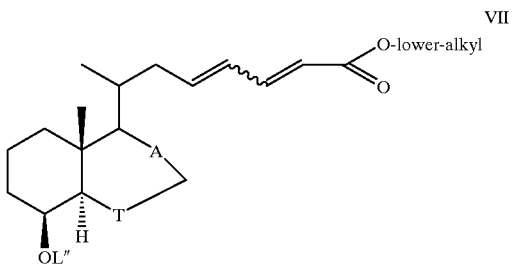

VII wherein L" is a silyl-protecting group, preferably TBDMS, via the alcohols of formula VIII

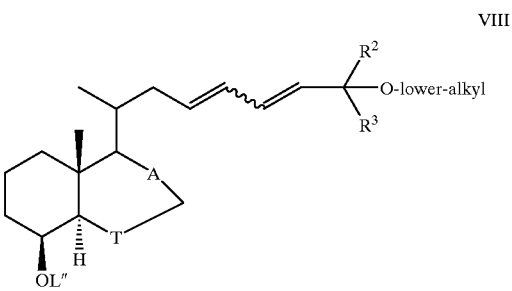

VIII

The conversion of the esters VII to the alcohols VIII can be performed in THF with CeCl$_3$, followed by reaction with methyllithium in ether at −78° C.

The deprotection of VIII to the diol V can be effected with TBAF in THF.

Alternatively, a silyl ether VII can first be deprotected, e.g. by reaction with aqueous hydrofluoric acid in THF, and the obtained ester-alcohol converted to the alcohol V in the same manner as described above for the conversion of the esters VII to the alcohols VIII.

The esters of formula VII can be obtained from aldehydes of formula IX

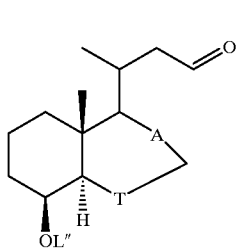

IX

Thus, a solution of trimethyl-4-phosphonocrotonate in THF can be reacted with lithium hexamethyldisilazide (LiHMDS) in THF at −78° C., and the obtained anion reacted at −40° C. with a solution of an aldehyde IX in THF.

Alternatively, the solution of trimethyl-4-phosphonocrotonate in THF is deprotonated at −78° C. with a solution of lithium diisopropylamide (LDA), obtained from diisopropylamine and n-butyllithium, in THF, and the obtained anion reacted at −78° C. with a solution of an aldehyde IX in THF.

The aldehydes IX can be obtained from alcohols of formula X

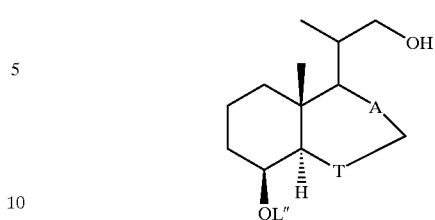

X by reaction with tosyl chloride in the presence of dimethylamino-pyridine in dichloromethane, then reacting the obtained tosylate with NaCN in dimethylsulfoxe (DMSO) at 90° C., and reacting the resulting cyanide with dibutylaluminium hydride (DIBAH) in dichloromethane at −10° C.

In a variant, which is preferred when A is a double bond, the alcohol of formula X is converted to the corresponding aldehyde, e.g. with Swern reagent, obtained from oxalyl chloride, DMSO and triethylamine. This aldehyde of formula XI

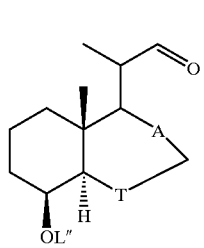

XI is reacted at −78° C. with an ylide solution, itself obtained by reaction of (methoxymethyl) triphenylphosphonium chloride in THF with n- or sec-butyllithium. The resulting enolether can then be hydrolyzed, e.g. with hydrochloric acid, to the aldehyde IX.

The alcohols X are known or can be obtained in a manner analogous to the known compounds.

An alcohol X with the non-natural configuration at the methylated C atom in position 20 of vitamin D$_3$, can be obtained by epimerization of the corresponding aldehyde XI with natural configuration, with 1,5-diaza-bicyclo[4.3.0]non-5-en (DBN) in THF, followed by reduction with sodium borohydride and chromatographic separation of the desired alcohol X.

Compounds of formula X wherein T is CH$_2$CH$_2$ can be prepared as described in the European patent application 0 771 789, as set forth in formula Scheme 1 below:

According to Scheme 1, compound (1) [Synthesis 957 (1993)] is reduced to yield the equatorial alcohol (2), which is transformed to (4) via the thiocarbamate (3). Compound (4) can be hydroborated to yield (5). Oxydation of the alcohol, e.g., with pyridiniumchlorochromate or TPAP and equilibration with potassium-t-butoxide yields (6), which can be reduced to give compound (7). Acetylation of (7) and cleavage of the tert.-butyl ether function yields (8) which is oxidized and deacylated to yield ketoalcohol (9). For build-up of the vitamin D$_3$ side chain the alcohol group of (9) is suitably protected, e.g., by a silyl ether protecting group Z, preferably the tert-butyl-dimethyl-silyl group, to obtain (10).

The ketone (10) is converted by a Wittig reaction into compound (11) from which (12) is obtained by an ene reaction with paraformaldehyde and dimethylaluminum chloride, or with paraformaldehyde and BF₃oEt₂O. Catalytic hydrogenation of (12) gives (13).

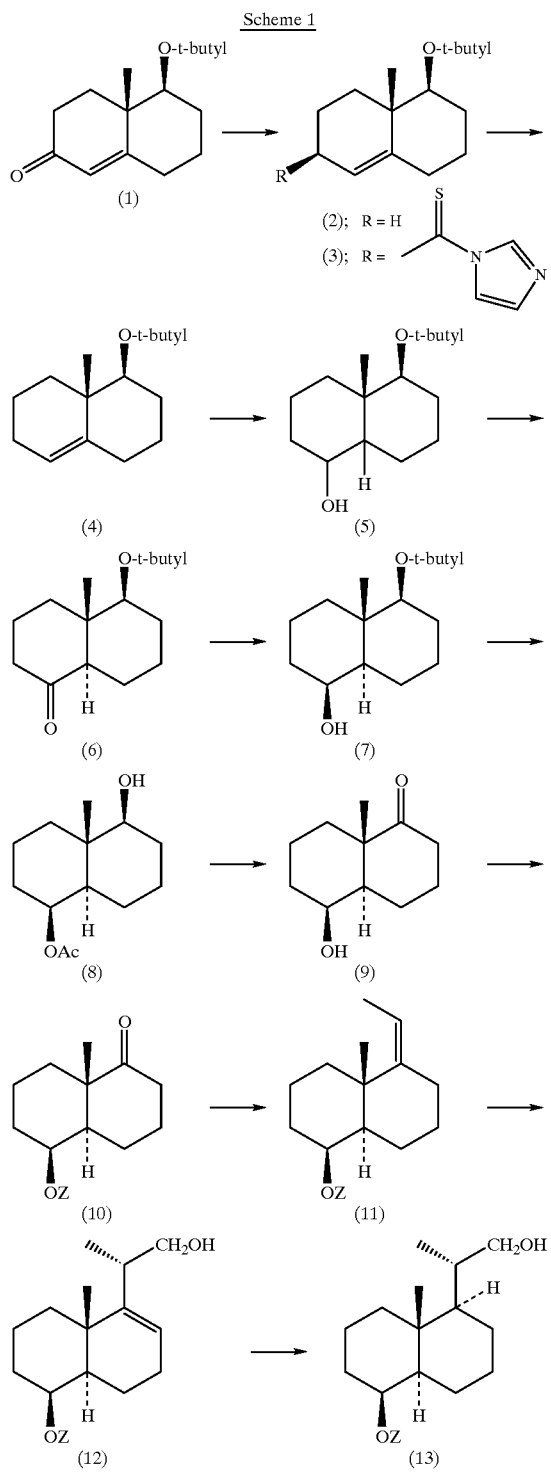

wherein Z is a hydroxy protecting group, preferably a silyl group as e.g. the tert.-butyldimethylsilyl group.

The phosphinoxydes of formula III are known or can be obtained in a manner analogous to the known compounds. Thus, those wherein X is CH₂ can be prepared as shown in formula Scheme 2 below:

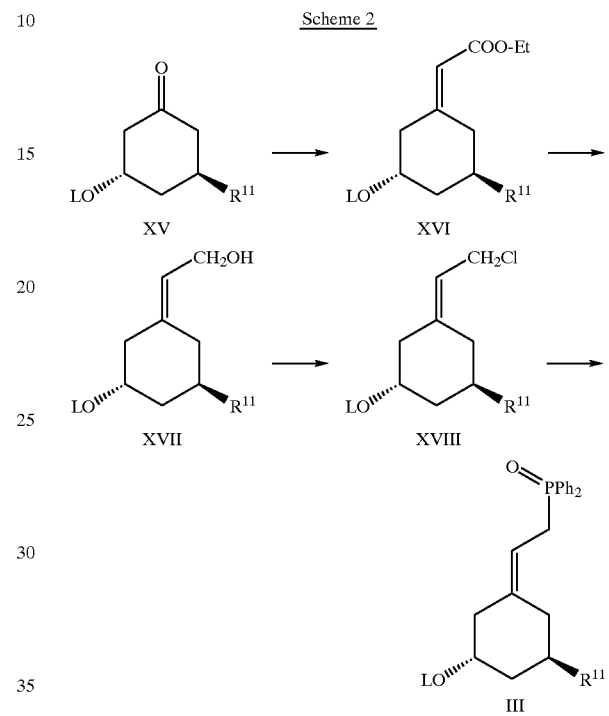

wherein L and $R^{11}$ are defined as above.

According to Scheme 2, the ketone XV is converted by a Peterson reaction into the ester XVI from which the alcohol XVII is obtained by reduction. Reaction of XVII with N-chlorosuccinimide in the presence of dimethylsulphur gives the chloride XVIII. Reaction of XVIII with diphenylphosphine-lithium and work-up with 5% H₂O₂ in ethyl acetate gives the phosphinoxide III'.

The reaction Scheme 3 below shows how the phosphinoxides III having the unnatural 3α-configuration can be prepared as described in Tetrahedron Letters 1992:2455 and 4364, and 1996:5589.

In Scheme 3, TBHP stands for tert-butyl-hydroperoxide, TBDPS for tert-butyl-diphenylsilyl, PPTS for pyridinium p-toluenesulfonate, Red-Al for sodium dihydro-bis(2-methoxyethoxy)aluminate, and NCS for N-chlorosuccinimide.

Scheme 3

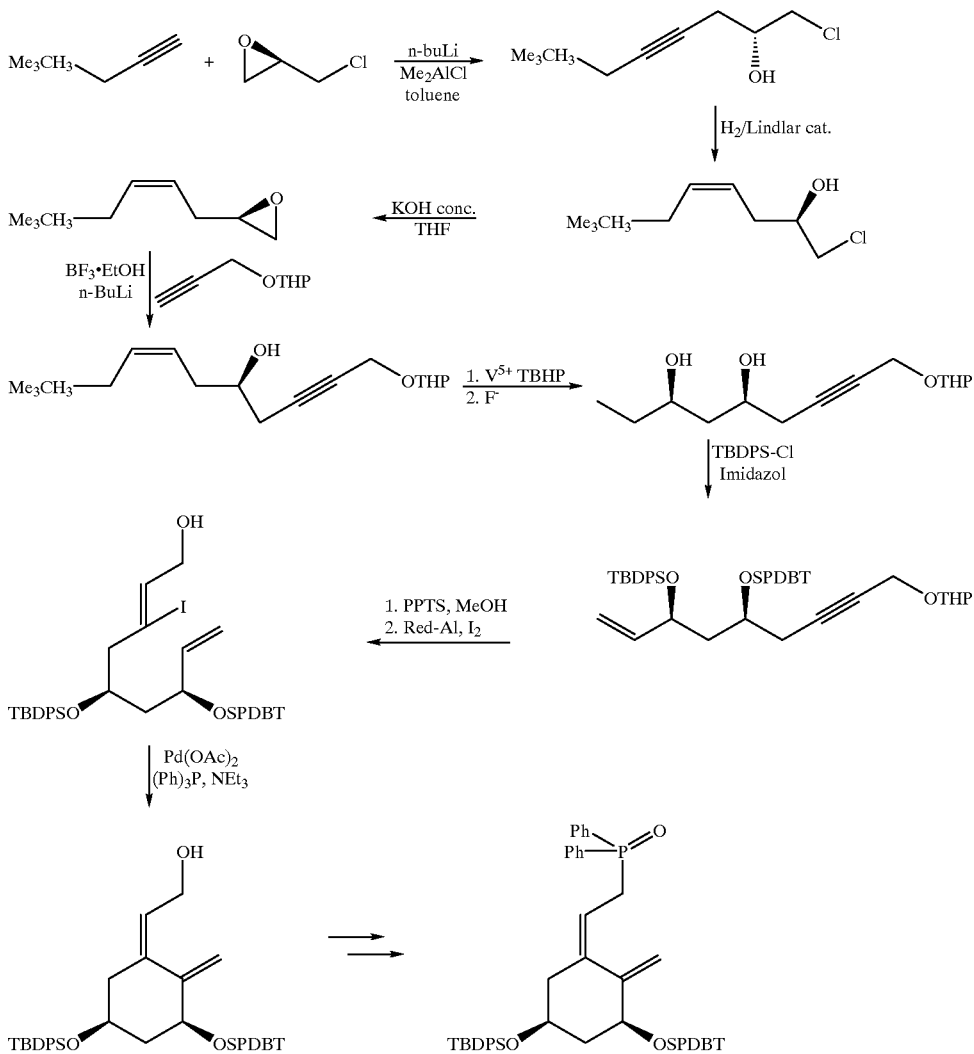

The compounds of formula II, wherein R⁴ is H and B² is C≡C can be obtained by deprotonation of a compound of formula XII

XII

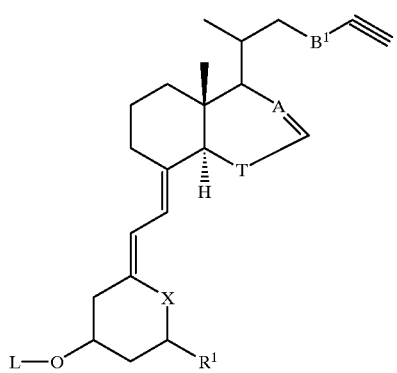

with a base, such as butyllithium, followed by the addition of a ketone of formula O=C(R², R³).

The compounds of formula II wherein B² is C≡C can be selectively reduced to those wherein B² is CH=CH, e.g. with lithiumaluminum-hydride in the presence of sodium methylate.

The compounds of formula XII can be obtained by Wittig-Horner coupling of a ketone of formula XIII

XIII

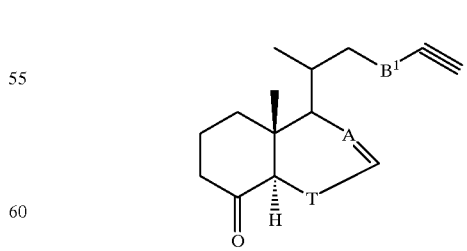

with a phosphinoxide of formula III, in the presence of a base, such as LiHMDS.

The ketones XIII can be obtained by deprotecting a compound of formula XIV

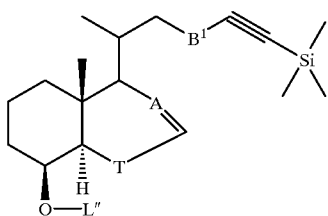

XIV

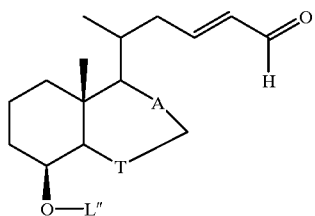

XVI for instance with hydrofluoric acid in THF/acetonitrile followed by oxidation of the obtained alcohol, e.g. with PDC in DMF.

The compounds of formula XIV wherein $B^1$ is CH=CH, can be obtained by Wittig-Horner reaction of the corresponding aldehyde of formula IX with 3-diethylphosphite-1-trimethylsilanyl-prop-1-yne, in the presence of LiHMDS.

The compounds of formula XIV wherein $B^1$ is C≡C can be obtained by treating the corresponding alcohol of formula X with triflic anhydride (trifluormethane-sulfonylanhydride) and reacting the resulting triflate by nucleophilic substitution (J.A.C.S. 119, 1997, 4353) with 4-trimethylsilylbutadiyne-1-lithium.

In a variant, alcohols of formula VIIIb

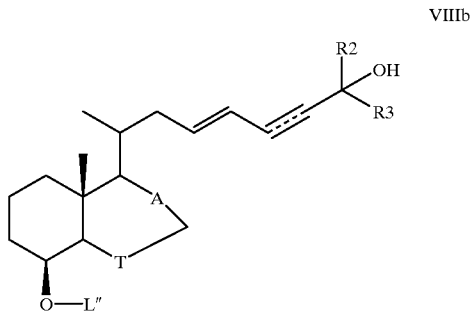

VIIIb can be obtained from the olefinic dibromides XV via Corey-Fuchs reaction, i.e. treatment with BuLi, followed by quenching of the resultant acetylide with the appropriate ketone and, if desired, selective reduction of the triple bond, e.g. with lithium aluminum hydride.

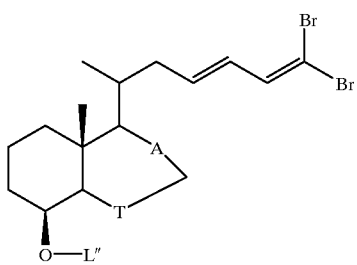

XV

The intermediates XV are available from the aldehydes XVI by a known method, namely reaction with triphenylphosphine and $CBr_4$ in $CH_2Cl_2$.

The latters can be synthesized from the aldehydes of formula IX by a highly E-selective Wittig-reaction with the stabilized ylide (carbetoxymethylene)triphenylphosphorane, ensuing reduction of the obtained α,β-unsaturated ester with DIBAL-H in THF and reoxidation with $MnO_2$ in $CH_2Cl_2$.

The intermediates of formula II and those of formulae IV, V and VI are also a further object of the present invention.

The following examples will, without limitation, illustrate the invention further.

EXAMPLE 1 a) The compound (S)-2-[(1R,3aR,4S,7aR)-4-(tert-Butyl-dimethylsilanyloxy)-7a-methyl-octahydro-inden-1-yl]-propan-1-ol (5.00 g; 15.31 mmol) is dissolved in dichloromethane (75 ml) at room temperature. Tosyl chloride (8.76 g; 45.93 mmol; 3 equivalents) and dimethyl-aminopyridine (5.61 g; 45.93 mmol; 3 equivalents) are added. The mixture is allowed to react over night. The reaction mixture is poured on brine and extracted with ethyl-acetate. The organic phase is dried over sodium sulfate and the solvents are removed. The crude tosylate is directly used in the next step. The intermediate tosylate is dissolved in DMSO (35 ml), NaCN (2.25 g; 45.93 mmol; 3 equivalents) is added and heated for 2 hours at 90° C. The reaction mixture is poured in water and extracted with hexane/ethyl-acetate 1:1. The organic phase is dried over sodium sulfate and the solvents are removed. The crude cyanide is directly used in the next step. The intermediate cyanide is dissolved in dichloromethane (50 ml), DIBAH is added slowly at −10° C. (38.3 ml of a 1.2 M solution; 45.93 mmol; 3 equivalents) and stirred for 2 hours at −10° C. The temperature is allowed to raise above the freezing point and a 1 M aqueous solution of ammonium chloride is added. After 10 minutes a 2:1 ether/1 N aqueous HCl (30 ml) is added and allowed to react for 15 minutes. The reaction mixture is extracted with ethyl-acetate. The organic phase is dried over sodium sulfate and the solvents are removed. After flash-chromatography (hexane/ethyl-acetate 95:5) (R)-3-[(1R,3aR,4S,7aR)-4(tert-Butyl-dimethylsilanyloxy)-7a-methyl-octahydro-inden-1-yl]-butan-1-al is obtained as a colorless waxy solid.

b) Trimethyl-4phosphonocrotonate (1.7 g; 8.2 mmol; 1.2 equivalents) is dissolved in anhydrous THF (20 ml). LiHMDS (8.2 ml of a 1 M solution in THF; 8.2 mmol; 1.2 equivalents) is added carefully at −78° C. After 15 minutes the reaction mixture is warmed up to −40° C. and (R)-3-[(1R,3aR,4S,7aR)-4-(tert-Butyl-dimethylsilanyloxy)-7a-methyl-octahydroinden-1-yl]-butan-1-al (2.3 g; 6.79 mmol) is added in solution in THF. After 15 minutes the reaction mixture is allowed to reach room temperature. The reaction mixture is then poured on brine and extracted with ethyl-acetate. The organic phase is washed with brine and dried over sodium sulfate. The solvents are removed and the crude mixture is chromatographed on silica-gel (eluent: n-hexane/ethyl-acetate 96/4).1.81 grams (63%) of pure E-isomer, (3E,5E)-(R)-6-[(1R,3aR,4S,7aR)-4-(tert-Butyldimethylsilanyloxy)-7a-methyl-octahydro-inden-1-yl]-octa-3,5-dienoic acid methyl ester is obtained in mixture with its Z-isomer (645 mg; 23%).

MS: (M—CH$_3$)$^+$ 405

IR: cm$^{-1}$ 3429; 2953; 2863; 1721; 1641; 1614; 1464; 1434; 1355; 1328; 1308; 1255; 1167; 1144; 1084; 1022; 1000; 973; 950; 925; 836; 773; 688.

c) (3E,5E)-(R)-6-[(1R,3aR,4S,7aR)-4-(tert-Butyl-dimethylsilanyloxy)-7a -methyl-octahydro-inden-1-yl]-octa-3,5-dienoic acid methyl ester (500 mg; 1.19 mmol) is dissolved in THF (20 ml) and aqueous hydrofluoric acid (40%) (10 ml) is added and stirred at room temperature over night. The reaction mixture is poured on a saturated solution of hydrogenocarbonate and extracted with ethyl-acetate. The organic phase is washed with brine and dried over sodium sulfate. The solvents are removed and the crude mixture is chromatographed on silica-gel (eluent: n-hexane/ethyl-acetate 75/25). One obtains 268 mg (74%) of the intermediate ester-alcohol, (3E,5E)-(R)-6-[(1R,3aR,4S,7aR)-4-hydroxy-7a-methyl-octahydro-inden-1-yl]-octa-3,5-dienoic acid methyl ester. This intermediate ester-alcohol (265 mg; 0.865 mmol) is dissolved in anhydrous THF (20 ml) and anhydrous cerium III chloride (704 mg; 2.85 mmol; 3.3 equivalents) is added. At −78° C. methyl-lithium (2.7 ml of a 1.6 M solution; 4.32 mmol; 5 equivalents) is added dropwise and the mixture is allowed to react for one hour. The reaction mixture is poured on chilled water and extracted with ethyl-acetate. The organic phase is washed with brine and dried over sodium sulfate. The solvents are removed and the crude mixture is chromatographed on silica-gel (eluent: n-hexane/ethyl-acetate 7/3). One obtains 199 mg (75%) of (3E,5E)-(1R,3aR,4S,7aR)-1-[(R)-7-hydroxy-1,7-dimethyl-octa-3,5-dienyl]-7a-methyl-octahydro-inden-4-ol as colorless crystals.

MP=110–112° C.

MS: (M)$^+$ 306

IR: cm$^{-1}$ 3394; 2969; 2943; 2880; 1652; 1627; 1451; 1372; 1232; 1166; 1135; 991; 942.

d) The compound (3E,5E)-(1R,3aR,4S,7aR)-1-[(R)-7-hydroxy-1,7-dimethyl-octa-3,5-dienyl]-7a-methyl-octahydro-inden-4-ol (180 mg; 0.587 mmol) was dissolved in DMF (6 ml). PDC (332 mg; 0.88 mmol; 1.5 equivalents) was added portion wise at room temperature, and the stirring was resumed for one hour. The reaction mixture was then poured on chilled brine, extracted twice with ethyl acetate, washed twice with brine, dried over anhydrous sodium sulfate and the solvent was removed. After flash-chromatography (eluent: hexane/ethyl-acetate 67/33) the hydroxyketone intermediate was obtained as a colorless oil. This intermediate was dissolved in dry THF (5 ml). Then, at 0° C. 1-trimethylsilyl-imidazol (61.6 μl; 0.42 mmol), imidazol (14.3 mg; 0.21 mmol; 0.5 equivalent) and trimethyl-silylchloride (26.6 μl; 0.21 mmol; 0.5 equivalent) were added sequentially. After twenty minutes at −0° C. the reaction mixture was allowed to reach slowly room temperature. The reaction mixture was then poured on chilled brine, extracted with ethyl acetate, washed with brine, dried over anhydrous sodium sulfate and the solvents were removed. After flash-chromatography (eluent: hexanes/ethyl-acetate 9/1) the compound (3E,5E)-(1R,3aR,7aR)-1-[(R)-1,7-dimethyl-7-trimethylsilanyloxy-octa-3,5-dienyl]-7a-methyl-octahydro-inden-4-one (105 mg; 51% yield) was obtained as a colorless oil.

MS: (M)$^+$ 376

NMR: (250 Mhz; CDCl$_3$; J═Hz): 6.12 (dd; J═15.2, 10.4; 1H), 6.01 (dd; J═14.8, 10.4; 1H); 5.68 (d; J═15.4; 1H); 5.64 (m; 1H); 2.46 (dd; J═12.5, 8.5; 1H); 2.32–1.32 (m; 14H); 1.34 (s; 6H); 0.97 (d; J═6.0; 3H); 0.65 (s; 3H); 0.12 (s; 9H).

e) The compound Z-(3S,5R)-[2-[3,5-bis-(tert-butyl-dimethyl-silanyloxy)-2-methylene-cyclohexylidene]-ethyl]-diphenyl-phosphine oxide (149 mg; 0.255 mmol; 2 equivalents) was dissolved in dry THF (3 ml). At −78° C. butyllithium (1.6 M in hexanes; 0.24 ml; 0.382 mmol; 3 equivalents) was slowly added. The reaction mixture turned to an intense red color and was stirred for 30 minutes. Then the compound (3E,5E)-(1R,3aR,7aR)-1-[(R)-1,7-dimethyl-7-trimethylsilanyloxy-octa-3,5-dienyl]-7a-methyl-octahydro-inden-4-one (48 mg; 0.127 mmol) was slowly added. After one hour at −78° C. the reaction mixture was allowed to reach slowly room temperature. The reaction mixture was then poured on chilled brine, extracted with ether, washed with brine, dried over anhydrous sodium sulfate and the solvents were removed. After flash-chromatography (eluent: hexane/ethyl-acetate 95/5) the compound (5Z,7E,23E,24aE)-(1R,3S)-1,3-bis-(tert-butyl-dimethyl-silanyloxy)-24a,24b-dihomo-25-trimethylsilanyloxy-9,10-seco-cholesta-5,7,10(19),23,24a-pentaene (58 mg; 61% yield) was obtained as a colorless foam.

f) The silylated compound (5Z,7E,23E,24aE)-(1R,3S)-1,3-bis-(tert-butyl-dimethyl-silanyloxy)-24a,24b-dihomo-25-trimethylsilanyloxy-9,10-seco-cholesta-5,7,10(19),23,24a-pentaene (54 mg; 0.073 mmol) was dissolved in a 1 molar solution of TBAF in THF (2 ml; 2 mmol; 10 equivalents) and stirred over night at room temperature. The reaction mixture was then poured on chilled brine, extracted with ethyl acetate, washed with brine, dried over anhydrous sodium sulfate and the solvent was removed. After flash-chromatography (eluent: hexane/isopropanol 73/27), the compound (5Z,7E ,23E,24aE)-(1R,3S)-24a,24b-dihomo-9,10-seco-cholesta- 5,7,10(19),23,24a-pentaene-1,3,25-triol was obtained as colorless crystals (29 mg; yield 90%).

MS: (M)$^+$ 440

IR: cm$^{-1}$ 3431; 2877; 1632; 1380; 1058; 996.

In analogy to Example 1 there were obtained:

EXAMPLE 2

(7E,23E,24aE)-(1R,3R)-24a,24b-Dihomo-19-nor-9, 10-seco-cholesta-5,7,23,24a-tetraene-1,3,25-triol,

MS: (M)$^+$ 428

IR: cm$^{-1}$ 3419; 2946; 2929; 2873; 2848; 1627; 1446; 1377; 1158; 1048; 989, using (3R,5R)-[2-[3,5-bis-(tert-butyl-dimethyl-silanyloxy)-cyclohexylidene]-ethyl]-diphenyl-phosphine oxide in the coupling reaction e),

EXAMPLE 3

(5Z,7E,23E,24aE)-(1S,3S)-24a,24b-Dihomo-9,10-seco-cholesta-5,7,10(19),23,24a-pentaene-1,3,25-triol,

MS: (M)$^+$ 440

IR: cm$^{-1}$3313; 2952; 2922; 2854; 1652; 1460; 1377; 1366; 1259; 1235; 1149; 1066; 1049; 1016; 989; 913, using (3S,5S)-[2-[3,5-bis-(tert-butyl-diphenyl-silanyloxy)-2-methylene-cyclohexylidene]-ethyl]-diphenyl-phosphine oxide in the coupling reaction e).

EXAMPLE 4 a) Swern reagent was prepared at −70° C. by adding slowly 1.70 ml of abs. DMSO to 0.947 ml of oxalylchloride, dissolved in 27 ml of $CH_2Cl_2$. 15 minutes later, 3.43 g of (S)-2-[(1R,4aR,5S,8aR)-5-(tert-butyldimethyl-silanyloxy)-8a-methyl-decahydro-naphthalen-1-yl]-propan-1-ol (synthesis described in ref. Ex. 12), dissolved in 10 ml of $CH_2Cl_2$, were slowly added. After 0.25 h, 4.8 ml of $NEt_3$ were added dropwise and the temperature allowed to reach −30° C. The reaction was quenched by pouring onto crushed ice/$NH_4Cl$, extracted with ether, washed with water and brine, dried over sodium sulfate and evaporated to dryness. Flash chromatography ($SiO_2$, hexane/AcOEt=97/3) afforded (S)-2-[(1R,4aR,5S,8aR)-5-(tert-butyldimethyl-silanyloxy)-8a-methyl-decahydro-naphthalen-1-yl]-propionaldehyde as colourless oil.

b) A suspension of 6.54 g of (methoxymethyl) triphenylphosphonium chloride in 38 ml of abs. THF was cooled to −10° and treated with 11.3 ml of nBuLi (1.5 M, hexane). 15 minutes later, the deep red ylide solution was cooled down to −78° and 3.225 g of (S)-2-[(1R,4aR,5S,8aR)-5-(tert-butyldimethyl-silanyloxy)-8a-methyl-decahydro-naphthalen-1-yl]-propionaldehyde dissolved in 21 ml of abs. THF, were slowly added and the reaction mixture kept for 60 minutes at that temperature. Partition between hexane and EtOH/$H_2O$=8/2, washing of the upper layer with EtOH/$H_2O$=8/2, drying over sodium sulfate, evaporating i. V. and flash chromatography ($SiO_2$, hexane/AcOEt=98/2) delivered 3.11 g of an enolether intermediate as E/Z-mixture, contaminated with some impurities which were removed after the next step. This enolether was hydrolyzed by dissolving it in 35 ml of THF containing 12.5 ml of 25% aq. HCl. After 2.5 h at ambient temperature, the reaction mixture was poured onto crushed ice, extracted with ether, washed with water and brine, dried over sodium sulfate and evaporated to dryness. Flash chromatography ($SiO_2$, hexane/AcOEt=98/2) yielded 1.76 g of (R)-3-[(1R,4aR,5S,8aR)-5-(tert-butyldimethyl-silanyloxy)-8a-methyl-decahydro-naphthalen-1-yl]-butyraldehyde as colourless oil.

c) A solution of lithium-diisopropylamide (LDA) was prepared from 11 mmol of diisopropylamine and 9.9 mmol of nBuLi (1.55 M, hexane) in 21 ml of abs. THF. After cooling to −78°, 2.22g of (E)-4-(dimethoxyphosphoryl)-but-2-enoic acid methyl ester dissolved in 10 ml of abs. THF, were added. Afterwards, 1.873 g of (R)-3-[(1R,4aR,5S,8aR)-5-(tert-butyldimethyl-silanyloxy)-8a-methyl-decahydro-naphthalen-1-yl]-butyraldehyde dissolved in 10 ml of abs. THF, were added and allowed to react for 1 h at −78°. The mixture was then poured onto crushed ice/$NH_4Cl$, extracted with ether, washed with water and brine, dried over sodium sulfate and evaporated to dryness. Flash chromatography ($SiO_2$, hexane/AcOEt=97/3) yielded 1.311 g of (2E,4E)-(R)-7-[(1R,4aR,5S,8aR)-5-(tert-butyldimethyl-silanyloxy)-8a-methyl-decahydro-naphthalen-1-yl]-octa-2,4-dienoic acid methyl ester as pale yellow oil, contaminated with trace amounts of the 2E, 4Z-isomer.

MS: $(M—CH_3)^+$ 419, (M-t-butyl)$^+$ 377.

d) 1.311 g of (2E,4E)-(R)-7-[(1R,4aR,5S,8aR)-5-(tert-butyldimethylsilanyloxy)-8a-methyl-decahydro-naphthalen-1-yl]-octa-2,4-dienoic acid methyl ester were dissolved in 35 ml of abs. THF. 2.45 g of anhydrous $CeCl_3$ were added and the mixture cooled down to −78°. Then, 6.0 ml of MeLi (1.5 M, ether) were injected by syringe. 1 h later, the reaction was quenched by pouring onto crushed ice/$NH_4Cl$, extracted with ether, washed with water and brine, dried over sodium sulfate and evaporated to dryness. Flash chromatography ($SiO_2$, hexane/AcOEt=8/2) yielded 954 mg of (3E,5E)-(R)-8-[(1R,4aR,5S,8aR)-5-(tert-butyldimethyl-silanyloxy)-8a-methyl-decahydro-naphthalen-1-yl]-2-methyl-nona-3,5-dien-2-ol as colourless oil.

MS: $(M)^+$ 434, $(M—H_2O)^+$ 416, (M-t-butyl)$^+$ 377.

e) 954 mg of (3E,5E)-(R)-8-[(1R,4aR,5S,8aR)-5-(tert-butyldimethylsilanyloxy)-8a-methyl-decahydro-naphthalen-1-yl]-2-methyl-nona-3,5-dien-2-ol were treated with 10 equivalents of anhydr. TBAF (2 M in THF) at 55° for 24 h. The reaction mixture was poured onto crushed ice/$NH_4Cl$, extracted with ether, washed with water and brine, dried over sodium sulfate and evaporated to dryness. Flash chromatography ($SiO_2$, hexane/AcOEt=7/3) yielded 685 mg of (1S,4aR,5R,8aR)-5-((3E,5E)-(R)-7-hydroxy-1,7-dimethyl-octa-3,5-dienyl)-4a-methyl-decahydro-naphthalen-1-ol as pale-yellow oil.

f) 459 mg of 4-methylmorpholine N-oxide, 40 mg of tetrapropylammonium perrhutenate, and 2.53 g of molecular sieves (powder, 4Å) were stirred for 0.25 h at ambient temperature. 590 mg of (1S,4aR,5R,8aR)-5-[(3E,5E )-(R)-(7-hydroxy-1,7-dimethyl-octa-3,5-dienyl)]-4a-methyl-decahydro-naphthalen-1-ol, dissolved in 5 ml of $CH_2Cl_2$, was added and the mixture kept for 2.5 h at RT. Dilution with ether, filtration over $SiO_2$, evaporation and flash chromatography ($SiO_2$, hexane/AcOEt=7/3) afforded 283 mg of (4aR,5R,8aR)-5-[(3E,5E)-(R)-(7-hydroxy-1,7-dimethyl-octa-3,5-dienyl)]-4a-methyl-octahydro-naphthalen]-1-one besides of 166 mg of a mixture of product and starting alcohol.

g) 323 mg of (4aR,5R,8aR)-5-((3E,5E)-(R)-7-hydroxy-1,7-dimethyl-octa-3,5-dienyl)-4a-methyl-octahydro-naphthalen-1-one, was reacted at 40° with 1.33 ml of TMS-imidazole (9 equivalents) in 8 ml of $CH_2Cl_2$. After a few hours the mixture was poured onto crushed ice, extracted with ether, washed with water, dried over sodium sulfate and evaporated to dryness. Flash chromatography ($SiO_2$, hexane/AcOEt=9/1) yielded 326 mg of (4aR,5R,8aR)-5-[(3E,5E)-(R)-(1,7-dimethyl-7-trimethylsilanyloxy-octa-3,5-dienyl)]-4a-methyl-octahydro-naphthalen-1-one as colourless oil.

MS: $(M)^+$ 390, $(M—CH_3)^+$375.

h) 597 mg of (Z)-(3S,5R)-[2-[3,5-bis-(t-butyldimethyl-silanyloxy)-2-methylene-cyclohexylidene]-ethyl]-diphenyl-phosphine oxide were dissolved in 10 ml of abs. THF and treated at −78° with 0.640 ml of nBuLi (1.6 M, hexane). After 10 minutes, 200 mg of (4aR,5R,8aR)-5-1(3E,5E)-(R)-(1,7-dimethyl-7-trimethylsilanyloxy-octa-3,5-dienyl)1-4a-methyl-octahydronaphthalen-1-one, dissolved in 0.5 ml of abs. THF, were added and the mixture kept for 0.5 h at −78° and for 0.5 h at 0°. After quenching with crushed ice/$KH_2PO_4$, the product was extracted with ether, washed with brine, dried over sodium sulfate and the solvents removed. Flash chromatography ($SiO_2$, hexane/AcOEt) yielded in the less polar fractions 91 mg of (5Z,7E,23E,24aE)-(1S,3R)-1,3-bis-(t-butyldimethyl-silanyloxy)-25-trimethylsilanyloxy-17a,24a,24b-trihomo-9,10-seco-cholesta- 5,7,10(19),23,24a-pentaene and in the more polare ones 149 mg of starting ketone. Finally, the excess of phosphine oxide was eluted with hexane/AcOEt=1/1.

i) 91 mg of (5Z,7E,23E,24aE)-(1S,3R)-1,3-bis-(t-butyldimethylsilanyloxy)-25-trimethylsilanyloxy-17a,24a,24b-trihomo-9,10-seco-cholesta-5,7,10(19),23,24a-pentaene were treated with 10 equivalents of anhydrous TBAF (1 M in THF) at 40° for 2 h. The reaction mixture was poured onto crushed ice/$NH_4Cl$, extracted with ether, washed with water, dried over sodium sulfate and evaporated to dryness. Flash chromatography ($SiO_2$, hexane/iPrOH=8/2) yielded 50 mg of (5Z,7E,23E,24aE)-(1S,3R)-17a,24a,24b-trihomo-9,10-seco-cholesta-5,7,10(19),23,24a-pentaene-1,3,25-triol as white foam.

MS: (M+1)+ 455, (M—H$_2$O)+ 436;

NMR: (1H, δ, TMS) 0.70 (s, 3H), 0.89 (d,3H), 1.33 (s, 6H), 1.1–2.1 (m, 20H), 2.15–2.35 (m, 2H), 2.61 (dd, 1H), 2.87 (br d, 1H), 4.24 (m, 1H), 4.43 (m, 1H), 5.00 (br s, 1H), 5.34 (br s, 1H), 5.57–5.75 (m, 2H), 5.91–6.04 (m, 2H), 6.18 (dd, 1H), 6.37 (d, 1H);

IR (cm$^{-1}$): 2925, 2855, 1052, 987.

EXAMPLE 5

(7E,23E,24aE)-(1R,3R)-17a,24a,24b-Trihomo-19-nor-9,10-seco-cholesta-5,7,23,24a-tetraene-1,3,25-triol was prepared in analogy to example 1, but using in step h) (3R,5R)-[2-[3,5-bis-(t-butyldimethyl-silanyloxy)-cyclohexylidene]-ethyl]-diphenylphosphine oxide.

MS: (M)+ 442, (M—H$_2$O)+ 424;

NMR: (1H, δ, TMS) 0.70 (s, 3H), 0.89 (d,3H), 1.33 (s, 6H), 1.1–2.05 (m, 21H), 2.22 (br qui, 2H), 2.49 (dxd, 1H), 2.70–2.91 (m, 2H), 4.06 (m, 1H), 4.14 (m, 1H) 5.63 (dxt, 1H), 5.69 (d, 1H), 5.83 (d, 1H), 5.97 (dxd, 1H), 6.18 (dxd, 1H), 6.31 (d);

IR (cm$^{-1}$): 2923, 2855, 1459, 1377.

EXAMPLE 6

(5Z,7E,23E,24aE)-(3S)-17a,24a,24b-Trihomo-9,10-seco-cholesta-5,7,10(19),23,24a-pentaene-3,25-diol was prepared in analogy to example 1, but using in step h) (Z)-(S)-[2-[5-(t-butyldimethyl-silanyloxy)-2-methylene-cyclohexylidene]-ethyl]-diphenylphosphine oxide.

MS: (M)+ 438, (M—H$_2$O)+ 420, (M—CH$_3$)+ 405;

NMR: (1H, δ, TMS) 0.70 (s, 3H), 0.89 (d,3H), 1.33 (s, 6H), 1.1–2.5 (m, 23H), 2.58 (dxd, 1H), 2.87 (br d, 11H), 3.94 (m, 1H), 4.81 (br s, 1H), 5.06 (br s, 1H), 5.64 (dxt, 1H), 5.69 (d, 1H), 5.92–6.05 (m, 2H), 6.13–6.27 (m, 2H).

EXAMPLE 7

(7E,23E,24aE)-(1R,3R)-17a,24a,24b-Trihomo-19-nor-9,10-seco-cholesta-5,7,17,23,24a-pentaene-1,3,25-triol was prepared as follows:

a) Swern reagent was prepared at –78° C. by adding slowly 1.6 ml of abs. DMSO, dissolved in 4 ml of CH$_2$Cl$_2$, to 0.908 ml of oxalylchloride in 26 ml of CH$_2$Cl$_2$.15 minutes later, 3.27 g of (S)-2-[(4aR,5S,8aS)-5-(tert-butyldimethyl-silanyloxy)-8a-methyl-3,4,4a,5,6,7,8,8a-octahydronaphthalen-1-yl]-propan-1-ol (synthesis described in ref. Ex. 12) dissolved in 11 ml of CH$_2$Cl$_2$, were slowly added. After 0.3 h, 4.6 ml of NEt$_3$ were added dropwise and the temperature allowed to reach –15° C. The reaction was quenched by pouring onto crushed ice/NH$_4$Cl, extracted with ether, washed with water and brine, dried over magnesium sulfate and evaporated to dryness. Flash chromatography (SiO$_2$, hexane/AcOEt=97/3) yielded (S)-2-[(4aR,5S,8aS)-5-(tert-butyldimethyl-silanyloxy)-8a-methyl-3,4,4a,5,6,7,8,8a-octa-hydro-naphthalen-1-yl]-propionaldehyde in nearly quantitative yield.

MS: M+ 336, (M-t-butyl)+ 279.

b) A suspension of 7.17 g of (methoxymethyl) triphenylphosphonium chloride in 50 ml of abs. THF was cooled to –20° and treated with 12.1 ml of nBuLi (1.55 M, hexane). 30 minutes later, the deep red ylide solution was cooled down to –78° and 3.525 g of (S)-2-[(4aR,5S,8aS)-5-(tert-butyldimethyl-silanyloxy)-8a-methyl-3,4,4a,5,6,7,8,8a-octa-hydronaphthalen-1-yl]-propionaldehyde dissolved in 21 ml of abs. THF, were slowly added and the reaction mixture kept for 45 minutes at that temperature. Partition between hexane and EtOH/H$_2$O=8/2, washing of the upper layer with EtOH/H$_2$O=8/2, drying over magnesium sulfate, evaporating i. V. and flash chromatography (SiO$_2$, hexane/AcOEt=99/1) generated 2.590 g of an enolether intermediate as E/Z-mixture. This enolether was hydrolyzed by dissolving it in 30 ml of THF containing 10 ml of 25% aq. HCl. After 90 minutes at ambient temperature, the reaction mixture was poured onto crushed ice, extracted with ether, washed with water and brine, dried over magnesium sulfate and evaporated to dryness. Flash chromatography (SiO$_2$, hexane/AcOEt=98/2) yielded 2.424 g of (R)-3-[(4aR,5S,8aS)-5-(tert-butyldimethyl-silanyloxy)-8a-methyl-3,4,4a,5,6,7,8,8a-octahydro-naphthalen-1-yl]-butyraldehyde as yellowish oil.

c) A LDA solution was prepared by adding at 0° 9.79 ml of nBuLi (1.55 M, hexane) to 2.30 ml of diisopropylamine. After cooling to –78°, 2.872 g of (E)-4-(dimethoxy-phosphoryl)-but-2-enoic acid methyl ester, dissolved in 17 ml of abs. THF, were added. 90 minutes later, 2.424 g of (R)-3-[(4aR,5S,8aS)-5-(tert-butyldimethyl-silanyloxy)-8a-methyl-3,4,4a,5,6,7,8,8a-octahydro-naphthalen-1-yl]-butyraldehyde dissolved in 15 ml of abs. THF, were added and allowed to react for 2 h at –78° and 1.5 h at –40°. The mixture was then poured onto crushed ice/NH$_4$Cl, extracted with ether, washed with brine, dried over magnesium sulfate, and evaporated to dryness. Flash chromatography (SiO$_2$, hexane/AcOEt=97/3), followed by MPLC (SiO$_2$, hexane/AcOEt=98.9/1.9) and crystallization from hexane, yielded 1.367 g of (2E,4E)-(R)-7-[(4aR,5S,8aS)-5-(tert-butyldimethyl-silanyloxy)-8a-methyl-3,4,4a,5,6,7,8,8a-octahydro-naphthalen-1-yl]-octa-2,4-dienoic acid methyl ester as white crystals of mp. 59–64°.

MS: M+ 432, (M-t-butyl)+ 375.

d) 1.365 g of (2E,4E)-(R)-7-[(4aR,5S,8aS)-5-(tert-butyldimethylsilanyloxy)-8a-methyl-3,4,4a,5,6,7,8,8a-octahydro-naphthalen-1-yl]-octa-2,4-dienoic acid methyl ester were dissolved in 75 ml of abs. THF. 2.566 g of anhydrous CeCl$_3$ were added and the resultant suspension cooled down to –78°. 6.9 ml of MeLi (1.6 M, ether) were added dropwise by syringe. 0.2 h later, the reaction was quenched by pouring onto crushed ice, extracted with AcOEt, washed with brine, dried over magnesium sulfate and evaporated i. V. Flash chromatography (SiO$_2$, hexane/AcOEt=9/1) yielded 1.250 g of (3E,5E)-(R)-8-[(4aR,5S,8aS)-5-(tert-butyldimethyl-silanyloxy)-8a-methyl-3,4,4a,5,6,7,8,8a octahydro-naphthalen-1-yl]-2-methyl-nona-3,5-dien-2-ol as colourless oil.

e) 1.245 g of (3E,5E)-(R)-8-[(4aR,5S,8aS)-5-(tert-butyldimethylsilanyloxy)-8a-methyl-3,4,4a,5,6,7,8,8a octahydro-naphthalen-1-yl]-2-methyl-nona-3,5-dien-2-ol were treated with 12 equivalents of anhydrous TBAF (1 M in THF) at 55° for 22 h. The reaction mixture was poured onto crushed ice/NH$_4$Cl, extracted with ether, washed brine, dried over magnesium sulfate and evaporated to dryness. Flash chromatography (SiO$_2$, hexane/AcOEt=7/3) delivered 929 mg of (1S,4aS,8aR)-5-[(3E,5E)-(R)-7-hydroxy-1,7-dimethyl-octa-3,5-dienyl)]-4a-methyl-1,2,3,4,4a,7,8,8a-octahydro-naphthalen-1-ol as colourless oil besides 62 mg of starting silyl ether.

f) 785 mg of 4-methylmorpholine N-oxide, 1.45 g of molecular sieves (powder, 4Å), and 925 mg of (1S,4aS,8aR)-5-[(3E,5E)-(R)-7-hydroxy-1,7-dimethyl-octa-3,5-dienyl)]-4a-methyl-1,2,3,4,4a,7,8,8a-octahydronaphthalen-1-ol dissolved in 16 ml of CH$_2$Cl$_2$ and 1.6 ml of acetonitrile, were stirred for 0.25 h. 102 mg of tetrapropylammonium perrhutenate were added and the mixture kept for 22 h at RT.

Dilution with ether, filtration over SiO₂, evaporation and flash chromatography (SiO₂, hexane/AcOEt=7/3) delivered 425 mg of (4aS,8aR)-5-[(3E,5E)-(R)-7-hydroxy-1,7-dimethyl-octa-3,5-dienyl)]-4a-methyl-3,4,4a,7,8,8a-hexahydro-2H-naphthalen- 1-one besides 99 mg of a mixture of product and starting secondary alcohol.

MS: M⁺ 316, (M—CH₃)⁺ 301.

g) 420 mg of (4aS,8aR)-5-((3E,5E)-(R)-7-hydroxy-1,7-dimethyl-octa-3,5-dienyl)-4a-methyl-3,4,4a,7,8,8a-hexahydro-2H-naphthalen-1-one were reacted at RT with 0.389 ml of TMS-imidazole (2 equivalents) in 1.3 ml of CH₂Cl₂. After 20 hours the mixture was poured onto crushed ice, extracted with ether, washed with brine, dried over magnesium sulfate and evaporated to dryness. Flash chromatography (SiO₂, hexane/AcOEt=95/5) yielded 463 mg of (4aS,8aR)-5-[(3E,5E)-(R)-(1,7-dimethyl-7-trimethylsilanyloxy-octa-3,5-dienyl)]-4a-methyl-3,4,4a,7,8,8a-hexahydro-2H-naphthalen-1-one as colourless oil.

MS: M⁺ 388, (M—CH₃)⁺ 373.

h) 820 mg of (3R,5R)-[2-[3,5-bis-(t-butyldimethyl-silanyloxy)-cyclohexylidene]-ethyl]-diphenyl-phosphine oxide were dissolved in 7.5 ml of abs. THF and treated at −78° with 1.0 ml of nBuLi (1.55 M, hexane). After 60 minutes, 310 mg of (4aS,8aR)-5-[(3E,5E)-(R)-(1,7-dimethyl-7-trimethylsilanyloxy-octa-3,5-dienyl)]-4a-methyl-3,4,4a,7,8,8a-hexahydro-2H-naphthalen-1-one dissolved in 1.5 ml of abs. THF, were added and the mixture kept for 0.75 h at −78° and for 0.5 h at 0°. After quenching with crushed ice/NH₄Cl, the product was extracted with ether, washed with water, dried over magnesium sulfate and the solvents removed i. V. Flash chromatography (SiO₂, hexane/AcOEt=98.5/1.5) yielded 191 mg of (7E,23E,24aE)-(1R,3R)-1,3-bis-(t-butyldimethyl-silanyloxy)-25-trimethylsilanyloxy-17a,24a,24b-trihomo-19-nor-9,10-seco-cholesta-5,7,17,23,24a-pentaene. Increasing the polarity (95/5) afforded in addition 182 mg of starting ketone.

i) 187 mg of (7E,23E,24aE)-(1R,3R)-1,3-bis-(t-butyldimethylsilanyloxy)-25-trimethylsilanyloxy-17a,24a,24b-trihomo-19-nor-9,10-seco-cholesta-5,7,17,23,24a-pentaene were treated with 13 equivalents of anhydr. TBAF (1 M in THF) at 45° for 2 h. The reaction mixture was poured onto crushed ice/NH₄Cl, extracted with ether, washed with water and brine, dried over sodium sulfate and evaporated to dryness. Flash chromatography (SiO₂, hexane/iPrOH=8/2) yielded 105 mg of (7E,23E,24aE)-(1R,3R)-17a,24a,24b-trihomo-19-nor-9,10-seco-cholesta-5,7,17,23,24a-pentaene-1,3,25-triol as white foam.

MS: M⁺ 440, (M—H₂O)⁺ 422;

NMR: (1H, δ, TMS) 0.76 (s, 3H), 1.01 (d,3H), 1.33 (s, 6H), 1.1–2.2 (m, 20H), 2.49 (dd, 1H), 2.75 (dd, 1H), 2.85 (m, 1H), 4.03 (m, 1H), 4.13 (m, 1H), 5.37 (m, 1H), 5.64 (dxt, 1H), 5.71 (d, 1H), 5.88 (d, 1H), 5.97 (dd, 1H), 6.17 (dd, 1H), 6.31 (d, 1H);

IR (cm⁻¹): 2922, 2854, 1455, 1376.

EXAMPLE 8

(5Z,7E,23E,24aE)-(1S,3R)-17a,24a,24b-Trihomo-9,10-seco-cholesta-5,7,10(19),17,23,24a-hexaene-1,3,25-triol was prepared in analogy to example 7, but using in step h) the (Z)-(3S,5R)-[2-[3,5-bis-(t-butyldimethyl-silanyloxy)-2-methylene-cyclohexylidene]-ethyl]-diphenyl-phosphine oxide.

MS: (M)⁺ 452, (M—H₂O)⁺ 434;

NMR: (1H, δ, TMS) 0.76 (s, 3H), 1.02 (d,3H), 1.33 (s, 6H), 1.0–2.25 (m, 18H), 2.32 (dd, 1H), 2.62 (dd, 1H), 2.89 (br d, 1H), 4.24 (m, 1H), 4.45 (m, 1H), 5.02 (br s, 1H), 5.35 (br s, 1H), 5.38 (m, 1H), 5.55–5.77 (m, 2H), 5.94–6.06 (m, 2H), 6.17 (dd, 1H), 6.39 (d, 1H); IR (cm⁻¹):

EXAMPLE 9

(5Z,7E,23E,24aE)-(1S,3S)-17a,24a,24b-Trihomo-9,10-seco-cholesta-5,7,10(19),17,23,24a-hexaene-1,3,25-triol was prepared in analogy to example 7, but using in step h) (Z)-(3S,5S)-[2-[3,5-bis-(t-butyldimethyl-silanyloxy)-2-methylene-cyclohexylidene]-ethyl]-diphenyl-phosphine oxide.

MS: (M+H)⁺ 453, (M—H₂O)⁺ 434;

NMR: (1H, δ, TMS) 0.76 (s, 3H), 1.02 (d, 3H), 1.33 (s, 6H), 1.2–2.7 (m, 19 H), 2.85 (br d, 1H), 4.06 (m, 2H), 4.33 (m, 1H), 5.02 (br s, 1H), 5.31 (br s, 1H), 5.35(m, 1H), 5.56–5.66 (m, 1H), 5.70 (d, 1H), 5.92–6.10 (m, 2H), 6.18 (dd, 1H), 6.44 (d, 1H).

EXAMPLE 10

(5Z,7E,23E,24aE)-(1S,3S)-17a,24a,24b-Trihomo-9,10-seco-cholesta-5,7,10(19),23,24a-pentaene-1,3,25-triol was prepared in analogy to example 4, but using in step h) (Z)-(3S,5S)-[2-[3,5-bis-(t-butyldimethyl-silanyloxy)-2-methylene-cyclohexylidene]-ethyl]-diphenyl-phosphine oxide.

MS: (M)⁺ 454, (M—HO)⁺ 437;

NMR: (1H, δ, TMS) 0.70 (s, 3H), 0.89 (d,3H), 1.33 (s, 6H), 1.2–2.3 (m, 20H), 2.44 (dd, 1H), 2.52–2.71 (m, 2H), 2.90 (br d, 1H), 4.06 (m, 1H), 4.33 (m, 1H), 5.02 (br s, 1H), 5.31 (br s, 1H), 5.56–5.70 (m, 1H), 5.70 (d, 1H), 5.92–6.05 (m, 2H), 6.17 (dd, 1H), 6.43 (d, 1H).

REFERENCE EXAMPLE 11

The phosphine oxide of formula III utilized in Examples 9 and 10 was obtained as follows:

a) 14.11 g (126 mmol) of propargyltrimethylsilane was dissolved in 125 ml of abs. toluene and cooled to −17°. 81.1 ml of nBuLi (1.55 M, hexane) was slowly added while keeping the temperature below −5°. 5 Minutes later, 126 ml of Me₂AlCl (1 M, hexane) was added to this solution of the Li-acetylide. The temperature was then lowered to −45° and 6.90 ml of (R)-epichlorohydrine (88 mmol), dissolved in 50 ml of toluene, was added. The cooling bath was then removed and the reaction mixture allowed to reach ambient temperature during 24h. After careful quenching with ice-cold water and filtration, the product was extracted with ether, washed with NH₄Cl, dried over sodium sulfate and the solvents removed i. V. Flash chromatography (SiO₂, hexane/AcOEt=86/14) yielded 12.01 g of (R)-1-chloro-6-trimethylsilanyl-hex-4-yn-2-ol as colorless oil, 97% pure according to GC.

MS: (M+H)⁺ 205, (M—CH₃)⁺ 189, (M—Cl)⁺ 169.

b) 13.04 g (63.7 mmol) of (R)-1-Chloro-6-trimethylsilanyl-hex-4yn-2-ol was dissolved in 260 ml of abs. EtOH and hydrogenated, in the presence of 9 drops of quinoline, over 1.70 g of Lindlar catalyst at ambient temperature and 1 atm of H₂. The progress of the reaction was followed by GC. After 2 h the reaction mixture was filtered and the solvent removed i.V. Short flash chromatography (SiO₂, hexane/AcOEt=85/15) afforded 12.97 g of (Z)-(R)-l-chloro-6-trimethylsilanyl-hex-4-en-2-ol as colorless oil.

MS: (M)⁺ 206, (M—HOSi(CH₃)₃)⁺ 116.

c) 12.97 g (62.7 mmol) of (Z)-(R)-1-Chloro-6-trimethylsilanyl-hex-4en-2-ol was dissolved in 215 ml of abs. THF. A solution of 60.34 g (1.08 mol) of KOH in 61 g of water was added ant the heterogeneous mixture stirred at 30° for 24 h, until GC analysis indicated the disappearance of the starting chlorohydrine. The reaction mixture was then poured onto crushed ice/NH$_4$Cl, extracted with ether, dried over sodium sulfate, and the solvents removed i.V. Thereby, 10.5 g of (Z)-(R)-trimethyl-(4-oxiranyl-but-2-enyl)silane was isolated, 93% pure according to GC, which was used as such for the next step.

d) 24.5 ml (174 mmol) of Tetrahydro-2-(2-propynyloxy) 2H-pyran was dissolved in 285 ml of abs. THF and deprotonated at −13°−−6° by adding slowly 112 ml of nBuLi (1.55 M, hexane). 20 Minutes later, the solution was cooled to −75° and 21.85 ml of BF$_3$oEtOEt was added. Afterwards, 10.51 g of (Z)-(R)-trimethyl-(4-oxiranyl-but-2-enyl)-silane, dissolved in 96 ml of abs. THF, was added within 75 minutes while maintaining the temperature below −70°. The reaction mixture was kept for another 50 minutes at this temperature and then poured onto crushed ice/NaHCO$_3$, extracted with ether, washed with brine, dried over sodium sulfate and evaporated to dryness. Flash chromatography (SiO$_2$, hexane/AcOEt=8/2) produced 17.83 g of (Z)-(5R)-9-(tetrahydro-pyran-2-yloxy)-1-trimethylsilanyl-non-2-en-7-yn-5-ol as colorless oil (1:1 epimeric mixture).

e) 17.83 g (57.4 mmol) of (Z)-(5R)-9-(tetrahydro-pyran-2-yloxy)-1-trimethylsilanyl-non-2-en-7-yn-5-ol was dissolved in 210 ml of abs. toluene. At −15°, 30.6 ml t-butyl-hydroperoxide (3 M, toluene) was added, followed by 761 mg (5 mol %) of vanadium-oxyacetylacetonate. The temperature was then rised within 16 h to 22°. TLC indicated the disappearance of starting olefin. While cooling in an ice bath, 13.5 ml (115 mmol) of trimethylphosphite was added in order to destroy the excess of hydroperoxide. 90 minutes later, a solution of 39.8 g of dry TBAF in 125 ml of THF was added and the reaction mixture kept for 90 minutes at RT. The homogeneous solution was then poured onto crushed ice, extracted with AcOEt, washed with water, dried over sodium sulfate and evaporated to dryness. Flash chromatography (SiO$_2$, hexane/AcOEt=6/4) yielded 10.40 g of (3S, 5S)-9-(tetrahydro-pyran-2-yloxy)-non-1-en-7-yne-3,5-diol as slightly yellow oil (1:1 epimeric mixture).

MS (CI): (M+NH$_4$)$^+$ 272, (M+Na)$^+$ 277.

f) 10.40 g (40.9 mmol) of (3S,5S)-9-(tetrahydro-pyran-2-yloxy)-non-1-en-7-yne-3,5-diol was dissolved in 30 ml of abs. DMF and treated successively with 18.9 g (6.8 eq.) of imidazole and 35.5 ml (3.4 eq.) of tert-butyl-chlorodiphenylsilane. After stirring for 20 h at 40°, the reaction mixture was poured onto crushed ice/EtOEt. Usual workup followed by flash chromatography (SiO$_2$, hexane/AcOEt=96/6) gave 25.16 g of (5S,7S)-2-[5,7-bis-(tert-butyl-diphenyl-silanyloxy)-non-8-en-2-ynyloxy]-tetrahydropyran as colorless oil (1:1 epimeric mixture).

g) 25.16 g (34.4 mmol) of (5S,7S)-2-[5,7-bis-(tert-butyl-diphenylsilanyloxy)-non-8-en-2-ynyloxy]-tetrahydro-pyran was deprotected by treatment at ambient temperature with 1.30 g (15 mol %) of pyridinium p-toluenesulfonate in 290 ml of abs. MeOH. The solution gradually became homogeneous. After 18 h the reaction mixture was quenched by pouring onto crushed ice/Na$_2$CO$_3$, extracted with ether, washed with water, dried over sodium sulfate and evaporated to dryness. Flash chromatography (SiO$_2$, hexane/AcOEt=82/18) yielded 19.17 g of (5S,7S)-5,7-bis-(tert-butyldiphenyl-silanyloxy)-non-8-en-2-yn-1-ol as yellowish crystals of mp. 114–116°.

MS: (M-t-butyl)$^+$ 589.

h) 6.80 (10.5 mmol) of (5S,7S)-5,7-bis-(tert-butyl-diphenyl-silanyloxy)-non-8-en-2-yn-1-ol was dissolved in 40 ml of abs. EtOEt and treated at 0° with 8.0 ml of Red-Al (3.5 M, toluene). After 90 minutes at RT, TLC indicated that some starting acetylene was still left. Additional 2 ml of Red-Al (3.5 M, toluene) was added and allowed to react for further 2 h. While cooling with an ice bath, 1.13 ml of AcOEt was injected in order to destroy the excessive reagent. The reaction flask was then cooled down to −75° and treated with a solution of 8.95 g (35 mmol) of 12 in 45 ml of THF. After 15 minutes, the cooling bath was removed and the reaction mixture quenched when the internal temperature had reached −25°, by pouring onto crushed ice/sodium pyrosulfite. Extraction with ether, washing with water, drying over sodium sulfate and evaporation of solvents left a crude product, which was purified by flash chromatography (SiO$_2$, hexane/AcOEt=83/17) to yield 3.99 g of (Z)-(5R,7S)-5,7-bis-(tert-butyl-diphenylsilanyloxy)-3-iodo-nona-2,8-dien-1-ol as a colorless gum.

MS (CI): (M+NH$_4$)$^+$ 792.

i) 3.99 g (5.15 mmol) of (Z)-(5R,7S)-5,7-bis-(tert-butyl-diphenylsilanyloxy)-3-iodo-nona-2,8-dien-1-ol was dissolved in 34 ml of abs. CH$_3$CN and treated under careful exclusion of oxygen with 7.2 ml (10 eq.) of NEt$_3$ and 595 mg (515 μmol) of (Ph$_3$P)$_4$Pd. The mixture was kept at 60° for 5 h and then poured onto crushed ice/NH$_4$Cl, extracted with ether, washed with NH$_4$Cl, dried over sodium sulfate and evaporated to dryness. Flash chromatography (SiO$_2$, hexane/AcOEt=83/17) delivered 2.95 g of (Z)-(3S,5S)-2-[3, 5-bis-(tert-butyl-diphenyl-silanyloxy)-2-methylenecyclohexylidene]-ethanol as reddish foam.

MS: (M—H2O)$^+$ 628, (M—HOCH$_2$)$^+$ 615, (M-t-butyl)$^+$ 589.

j) 1.31 g (9.81 mmol) of N-chloro-succinimide in 34 ml of abs. CH$_2$Cl$_2$ was treated at −10° with 749 μl (10.2 mmol) of dimethyl sulfide. 15 Minutes later, 2.95 g (4.559 mmol) of (Z)-(3S,5S)-2–13,5-bis-(tert-butyl-diphenyl-silanyloxy)-2-methylene-cyclohexylidenel-ethanol, dissolved in 10 ml of CH$_2$Cl$_2$, was slowly added to the resultant white suspension at the same temperature and then stirred for additional 30 minutes at RT. The reaction mixture was then poured onto crushed ice, extracted with ether, washed with water, dried over sodium sulfate and evaporated to dryness. Flash chromatography (SiO$_2$, hexane/AcOEt=97.5/2.5) yielded 2.76 g of (Z)-(3S,5S)-1-(2-chloro-ethylidene)-3,5-bis-(tert-butyl-diphenyl-silanyloxy)-2-methylene-cyclohexane as yellowish foam.

k) 847 μl (10.2 mmol) of diphenylphosphine in 16 ml of abs. THF was deprotonated at −10° with 3.05 ml nBuLi (1.5 M, hexane). The solution was then cooled to −75° and 2.76 g (4.15 mmol) of (Z)-(3S,5S)-1-(2-chloroethylidene)-3,5-bis-(tert-butyl-diphenyl-silanyloxy)-2-methylenecyclohexane, dissolved in 16 ml of abs. THF, was added dropwise. 10 Minutes later, 190 μl of water was injected and the reaction mixture allowed to reach room temperature. All solvents were then removed i.V., the residue taken up in 33 ml of CH$_2$Cl$_2$ and treated with 81 ml of 5% H$_2$O$_2$. After stirring for 75 minutes, the layers were separated, the aqueous phase extracted with AcOEt, the organic layers washed with sodium pyrosulfite, dried over sodium sulfate and evaporated to dryness. Flash chromatography (SiO2, hexane/AcOEt=45/55) afforded 2.534 g of (Z)-(3S,5S)-[2[-3,5-bis-(tert-butyl-diphenyl-silanyloxy)-2-methylenecyclohexylidene]-ethyl]-diphenyl-phosphine oxide as colorless foam.

MS: (M)$^+$ 830, (M-t-butyl)$^+$ 773.

NMR: (1H, δ, TMS) 0.94 (s, 9H), 1.04 (s, 9H), 1.96 (m, 1H), 2.11 (m, 1H), 2.89–3.05 (m, 2H), 3.11 (m, 1H), 3.36

(m, 1H), 4.73 (br s, 1H), 5.15 (q, 1H), 5.42 br s, 1H), 7.06 (dxt, 2H), 7.23–7.62 (m, 30 H).

REFERENCE EXAMPLE 12

The alcohol-ethers of formula X utilized as starting materials in the above Examples 4a) and 7a) were obtained as described in Examples 1 to 14 of the European patent application 0 771 789, i.e. starting from (4aS,5S)-5-tert-butoxy-4a-methyl-4,4a,5,6,7,8-hexahydro-2(3H)-naphtalenone, via:
a) (2S,4aS,5S)-5-tert-butoxy-4a-methyl-2,3,4,4a,5,6,7,8-octahydronaphtalen-2-ol,
b) imidazole-1-carbothioic acid(2S, 4aS, 5S)-O-(5-tert-butoxy-4a-methyl-2,3,4,4a,5,6,7,8-octahydro-naphtalen-2-yl)ester,
c) (4S,4aS)-4-tert-butoxy-4a-methyl-1,2,3,4,4a,5,6,7-octahydronaphtalene,
d) (1S,4aS,5S,8aS)- and (1R,4aS,5S,8aR)-5-tert-butoxy-4a-methyl-decahydro-naphtalen-1-ol,
e) (4aS,5S,8aR)-5-tert-butoxy-4a-methyl-octahydro-naphtalen-1-one,
f) (1S, 4aS, 5S, 8aR)-5-tert-butoxy-4a-methyl-decahydro-naphtalen-1-ol,
g) acetic acid(1S,4aS,5S,8aR)-5-tert-butoxy-4a-methyl-decahydronaphtalen-1-yl ester,
h) acetic acid (1S, 4aS, 5S,8aR)-5-hydroxy-4a-methyl-decahydronaphtalen-1-yl ester,
i) acetic acid (1S,4aS,8aR)-4a-methyl-5-oxo-decahydronaphtalen-1-yl ester,
j) (4aR,5S,8aS)-5-hydroxy-8a-methyl-octahydro-naphtalen-1-one,
k) (4aR,5S,8aS)-5-(tert-butyl-dimethyl-silanyloxy)-8a-methyl-octahydronaphtalen-1-one,
l) (1S,4aS,8aR)-tert-butyl-(5-ethylidene-4a-methyl-decahydronaphtalen-1-yloxy)-dimethyl-silane,
m) (S)-2-[(4aR,5S,8aS)-5-(tert-butyl-dimethyl-silanyloxy)-8a-methyl-3,4,4a,5,6,7,8,8a-octahydro-naphtalen-1-yl]-propan-1-ol, and
n) (S)-2-[(1R,4aR,5S,8aR)-5-(tert-butyl-dimethyl-silanyloxy)-8a-methyldecahydro-naphtalen-1-yl]-propan-1-ol.

EXAMPLE 13

The Wittig-Horner reaction of the aldehyde of formula IX, (R)-3-[(1R,3aR,4S,7aR)-4-(tert-butyl-dimethylsilanyloxy)-7a-methyl-octahydroinden-1-yl]-butan-1-al, with 3-diethylphosphite-1-trimethylsilanyl-prop-1-yne affords the compound of formula XIV, (1R,3aR,4S,7aR)-4-(tert-butyl-dimethylsilanyloxy)-1-[(R)-1-methyl-6-trimethylsilanyl-hexa-3-ene-5-ynyl]-7a-methyl-octahydro-indene in a 2:1 E/Z mixture in 83% yield. After removal of the silyl-groups (aequeous HF in THF/acetonitrile), the resulting secondary alcohol was oxidized with PDC in DMF to afford the ketone of formula XIII, (1R,3aR,7aR)-1-[(R)-1-methyl-hexa-3-ene-5-ynyl]-7a-methyl-octahydro-inden-4-one in a 1:1 E/Z mixture in 45% yield.

The Wittig-Horner coupling of this ketone with the A-ring, (3R,5R)-[2-[3,5-bis-(tert-butyl-dimethyl-silanyloxy)-cyclohexylidene]-ethyl]-diphenyl-phosphine oxide, affords the intermediate of formula XII, (7E)-(1R, 3R)-1,3-bis-(tert-butyl-dimethyl-silanyloxy)-19,27-dinor-9,10-seco-cholesta-5,7,23-trien-25-yne in a 1:1 23E/Z mixture in 86% yield.

After deprotonation of this intermediate and addition of a ketone of formula O=C($R^2$,$R^3$), e.g. acetone, hexafluoroacetone, cyclopentanone; or 3-pentanone, and removal of the silyl-groups (TBAF in THF), one obtains the following ene-yne derivatives:
a) 1:1 mixture of (7E,23E)- and (7E,23Z)-(1R,3R)-24a,24b-dihomo-19-nor-9,10-seco-cholesta-5,7,23-trien-24a-yne-1,3,25-triol,
b) 1:1 mixture of (7E,23E)- and (7E,23Z)-(1R,3R)-24a,24b,26a-26b-tetrahomo-19-nor-9,10-seco-cholesta-5,7,23-trien-24a-yne-1,3,25-triol,
c) 1:1 mixture of (7E,23E)- and (7E,23Z)-(1R,3R)-25-(1-hydroxy-cyclopentyl)-24a,24b-dihomo-19-nor-9,10-seco-cholesta-5,7,23-trien-24a-yne-1,3,25-diol,
d) 2:1 mixture of (7E,23E)- and (7E,23Z)-(1R,3R)-26,26,26,27,27,27-hexafluoro-24a,24b-dihomo-19-nor-9,10-seco-cholesta-5,7,23-trien-24a-yne-1,3,25-triol.

These ene-yne derivatives can be transformed to the corresponding diene derivatives by treatment with LiALH4 in presence of MeONa:
e) 1:1 mixture of (7E,23E24aE)- and (7E,23Z,24aE)-(1R, 3R)-24a,24b,26a,26b-tetrahomo-19-nor-9,10-seco-cholesta-5,7,23,24a-tetraen-24a-yne-1,3,25-triol,
f) 1:1 mixture of (7E,23E,24aE)- and (7E,23Z,24aE)-(1R, 3R)-25-(1-hydroxy-cyclopentyl)-24a,24b-dihomo-19-nor-9,10-seco-cholesta-5,7,23,24a-tetraen-24a-yne-1,3, 25-diol,
g) 2:1 mixture of (7E,23E,24aE)- and (7E,23Z,24aE)-(1R, 3R)-26,26,26,27,27,27-hexafluoro-24a,24b-dihomo-19-nor-9,10-seco-cholesta-5,7,23,24a-tetraen-24a-yne-1,3, 25-triol.

Pharmaceutical properties of the compounds of formula I can be determined according to the following procedures:

In vitro Assay for IL-12 Inhibition

THP-1 cells were obtained from American Tissue Culture Collection and cultured in complete medium. To assay for IL-12 production, THP-1 cells, $1.25 \times 10^6$ cells/ml, were stimulated with *S. aureus* Cowan strain (SAC) and human recombinant interferon-γ (huIFN-γ), (1000 U/ml). Alternatively, 1:6 diluted human peripheral whole blood (1 ml culture in 48 well plates) was primed with huIFN-γ (1000 U/ml), for 16 hours at 37° C., and then stimulated with SAC. Culture supernatants were collected after 48 hours, and freezed at −20° C. until assayed.

IL-12 production was measured by specific Enzyme Linked Immuno Sorbant Assay (ELISA), using 20C2 antibody (rat anti human IL-12 heterodimer p40-p35), at 2.5 μg/ml in coating buffer, and peroxidase-conjugated 4D6 antibody (rat anti human IL-12) at 250 ng/ml in assay buffer (as described in Zhang, M., M. K. Gately, E. Wang, J. Gong, S. F. Wolf, S. Lu, R. L. Modlin, and P. F. Barnes, 1994, Interleukin 12 at the site of disease in tuberculosis, J. Clin. Invest. 93:1733–1739). Standard (recombinant human IL-12, 800 pg/ml to 6 pg/ml) and samples containing culture supernatants (100 μl), diluted in assay buffer were added to duplicate wells. Absorbance was read at 450–650 nm. The unknown IL-12 concentrations of the samples were read from the corresponding standard curve and multiplied by the corresponding dilution factor. Maximal IL-12 production varies between 200 and 400 pg/ml.

Lyophilized vitamin $D_3$ analogs were diluted in EtOH in the dark and in the cold at a concentration of 2 mM. Serial dilutions (1 μM–1 pM) were prepared in EtOH. 10 μl of each dilution was added to 1 ml culture. $IC_{50}$ values for the inhibition of IL-12 production by the vitamin $D_3$ analogs are reported in the following table:

| Example | IC50 (nM) |
| --- | --- |
| 1 | 10 |
| 3 | 30 |
| 4 | 1 |
| 8 | 1 |
| 13a | 10 |
| 13c | 10 |
| 13d | 10 |
| 13e | 1 |
| 13f | 10 |
| Calcitriol | 60 |

From the above results, it can be seen that the compounds of formula I efficiently inhibit IL-12 production in vitro.

Accordingly, the compounds of formula I are useful in the prevention and treatment of IL-12-dependent autoimmune diseases such as rheumatoid arthritis, psoriasis, insulin-dependent diabetes mellitus, multiple sclerosis, inflammatory bowel disease, septic shock and allergic encephalomyelitis.

The compounds of formula I as described above can be administered orally, for the treatment of hyperproliferative skin diseases such as psoriasis, basal cell carcinomas, disorders of keratinization, and keratosis, or for the treatment of neoplastic diseases such as leukemia, or for the treatment of diseases which require modulation of the immune system, such as multiple sclerosis, transplant rejection, graft vs. host disease, or for the treatment of osteoporosis and hyperparathyroidism, to warmblooded animals which need such treatment. More specifically, the compounds of formula I as described above can be administered orally to an adult human in dosages that are in the range of about 0.5 to 1000 μg per day for the treatment of the above diseases.

The compounds of formula I can be administered orally for the prevention and treatment of IL-12-dependent autoimmune diseases, such as rheumatoid arthritis, psoriasis, insulin-dependent diabetes mellitus, multiple sclerosis, inflammatory bowel disease, septic shock and allergic encephlaomyelitis, to warm blooded animals which need such treatment;

they can be administered orally to adult humans in dosages in the range of 0.5 to 1000 pg per day.

The compounds of formula I as described above can be administered topically, for the treatment of hyperproliferative skin diseases such as psoriasis, to warmblooded animals which need such treatment. More specifically, the compounds of formula I as described above can be administered topically in dosages that are in the range of about 0.5 to 1000 μg per gram of topical formulation per day, for the treatment of the above diseases.

The dosage of the compounds of formula I can vary within wide limits depending on the illness to be treated, the age and the individual condition of the patient and on the mode of administration and will, of course, be fitted to the individual requirements in each particular case.

Oral dosage forms comprising compounds of formula I of the invention may be incorporated in capsules, tablets and the like with pharmaceutically acceptable carrier materials. Illustrative of such carrier materials which may be incorporated into capsules, and the like are the following: an emulsifier such as polyethylene glycol; a solubilizer such as a short chain triglyceride, e.g. Miglyol; a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I of the invention include: ointments and creams encompassing formulations having oleaginous, absorbable, water-soluble and emulsion-type bases such as petrolatum, lanolin, polyethylene glycols and the like. Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like. Gels are semisolid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of the disorder for the exertion of local action. Accordingly, the topical composition include those pharmaceutical forms in which the compound is applied externally by direct contact with the skin. The topical dosage forms comprise gels, creams, lotions, ointments, powders, aerosols and other conventional forms for applying medication to the skin obtained by admixing the compounds of formula I with known pharmaceutical topical carrier materials.

The following pharmaceutical compositions can be prepared in a known manner:

EXAMPLE A

| Soft Gelatine Capsule | mg/Capsule |
| --- | --- |
| Compound I | 0.0001–1 |
| Butylated Hydroxytoluene (BHT) | 0.016 |
| Butylated Hydroxyanisole (BHA) | 0.016 |
| Fractionated Coconut Oil (Neobee M-5) or Miglyol 812 q.s. | 160.0 |

EXAMPLE B

| Soft Gelatine Capsule | mg/Capsule |
| --- | --- |
| Compound I | 0.0001–1 |
| α-Tocopherol | 0.016 |
| Miglyol 812 q.s. | 160.0 |

EXAMPLE C

| Topical Cream | mg/g |
|---|---|
| Compound I | 0.005–1 |
| Cetyl Alcohol | 1.5 |
| Stearyl Alcohol | 2.5 |
| Span 60 (Sorbitan monostearate) | 2.0 |
| Arlacel 165 (Glyceryl monostearate and polyoxyethylene glycol stearate blend) | 4.0 |
| Tween 60 (polysorbate 60) | 1.0 |
| Mineral Oil | 4.0 |
| Propylene Glycol | 5.0 |
| Propylparaben | 0.05 |
| BHA | 0.05 |
| Sorbitol Solution | 2.0 |
| Edetate Disodium | 0.01 |
| Methylparaben | 0.18 |
| Distilled Water | q.s. |

We claim:

1. A polyunsaturated 24a,24b-dihomo-9,10-secocholestane derivative of formula I:

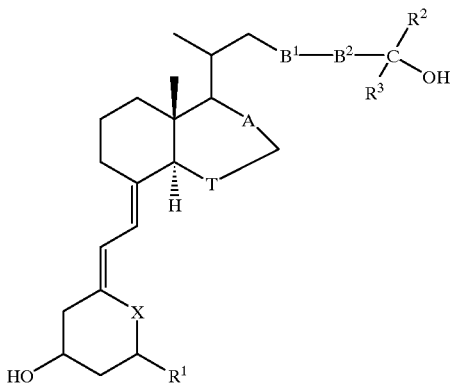

wherein

A is a single or double bond, $B^1$ is CH═CH, $B^2$ is CH═CH or C≡C,

T is $CH_2$ or $CH_2CH_2$,

X is $CH_2$— or >C═$CH_2$, $R^1$ is H, F or OH, $R^2$ and $R^3$ are each independently $C_{1-4}$-alkyl or $CF_3$, or $C(R^2 \cdot R^3)$ is $C_{3-6}$-cycloalkyl.

2. A compound of claim 1, wherein $R^1$ is H or OH.

3. A compound of claim 2, wherein the side chain is:

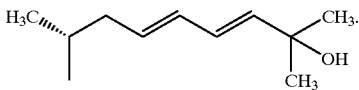

4. A compound of claim 3, (5Z,7E,23E,24aE)-(1R,3S)-24a,24b-dihomo-9,10-seco-cholesta-5,7,10(19),23,24a-pentaene-1,3,25-triol.

5. A compound of claim 3, (7E,23E,24aE)-(1R,3R)-24a,24b-dihomo-19-nor-9,10-seco-cholesta-5,7,23,24a-tetraene-1,3,25-triol.

6. A compound of claim 3, (5Z,7E,23E,24aE)-(1S,3S)-24a,24b-dihomo-9,10-seco-cholesta-5,7,10(19),23,24a-pentaene-1,3,25-triol.

7. A compound of claim 3, (5Z,7E,23E,24aE)-(1S,3R)-17a,24a,24b-trihomo-9,10-seco-cholesta-5,7,10(19),23,24a-pentaene-1,3,25-triol.

8. A compound of claim 3, (7E,23E,24aE)-(1R,3R)-17a,24a,24b-trihomo-19-nor-9,10-seco-cholesta-5,7,23,24a-tetraene-1,3,25-triol.

9. A compound of claim 3, (5Z,7E,23E,24aE)-(3S)-17a,24a,24b-trihomo-9,10-seco-cholesta-5,7,10(19),23,24a-pentaene-3,25-diol.

10. A compound of claim 3, (7E,23E,24aE)-(1R,3R)-17a,24a,24b-trihomo-19-nor-9,10-seco-cholesta-5,7,17,23,24a-pentaene-1,3,25-triol.

11. A compound of claim 3, (5Z,7E,23E,24aE)-(1S,3R)-17a,24a,24b-trihomo-9,10-seco-cholesta-5,7,10(19),17,23,24a-hexaene-1,3,25-triol.

12. A compound of claim 3, (5Z,7E,23E,24aE)-(1S,3S)-17a,24a,24b-trihomo-9,10-seco-cholesta-5,7,10(19),17,23,24a-hexaene-1,3,25-triol.

13. A compound of claim 3, (5Z,7E,23E,24aE)-(1S,3S)-17a,24a,24b-trihomo-9,10-seco-cholesta-5,7,10(19),23,24a-pentaene-1,3,25-triol.

14. A compound of claim 3, (7E,23E,24aE)-(1R,3R)-24a,24b-Dihomo-19-nor-9,10-seco-cholesta-5,7,16,23,24a-pentaene-1,3,25-triol.

15. A compound of claim 3, (5Z,7E,23E,24aE)-(1S,3R)-24a,24b-Dihomo-9,10-seco-cholesta-5,7,10(19),16,23,24a-hexaene-1,3,25-triol.

16. A compound of claim 3, (5Z,7E,23E,24aE)-(3S)-24a,24b-Dihomo-9,10-seco-cholesta-5,7,10(19),16,23,24a-hexaene-3,25-diol.

17. A compound of claim 1 wherein $B^1$ is —CH═CH— and $B^2$ is —C≡C—, in which the side chain is:

18. A compound according to claim 17, (7E,23E)-(1R,3R)-17a,24a,24b-Trihomo-19-nor-9,10-seco-cholesta-5,7,23-triene-24a-yne-1,3,25-triol.

19. A compound according to claim 17, (5Z,7E,23E)-(1S,3R)-17a,24a,24b-Trihomo-9,10-seco-cholesta-5,7,10(19),23-tetraene-24a-yne-1,3,25-triol.

20. A compound according to claim 17, (7E,23E)- and (7E,23Z)-(1R,3R)-24a,24b-dihomo-19-nor-9,10-seco-cholesta-5,7,23-trien-24a-yne-1,3,25-triol.

21. A compound according to claim 17, (7E,23E)- and (7E,23Z)-(1R,3R)-24a,24b,26a,26b-tetrahomo-19-nor-9,10-seco-cholesta-5,7,23-trien-24a-yne-1,3,25-triol.

22. A compound according to claim 17, (7E,23E)- and (7E,23Z)-(1R,3R)-26,26,26,27,27,27-hexyfluoro-24a,24b-dihomo-19-nor-9,10-seco-cholesta-5,7,23-trien-24a-yne-1,3,25-triol.

23. A compound according to claim 17, (7E,23E,24aE)- and (7E ,23Z,24aE)-( 1R,3R)-24a,24b,26a,26b-tetrahomo-19-nor-9,10-seco-cholesta-5,7,23,24a-tetraen-24a-yne-1,3,25-triol.

24. A compound according to claim 17, (7E,23E,24aE)- and (7E,23Z,24aE)-(1R,3R)-26,26,26,27,27,27-hexafluoro-24a,24b-dihomo-19-nor-9,10-seco-cholesta-5,7,23,24a-tetraen-24a-yne-1,3,25-triol.

25. A compound of claim 1 wherein $B^1$ is —CH═CH—, $B^2$ is —C≡C— and $C(R^2, R^3)$ is $C_{3-6}$-cycloalkyl.

26. A compound of claim 25, (7E,23E)- and (7E,23Z)-(1R,3R)-25-(1-hydroxy-cyclopentyl)-24a,24b-dihomo-19-nor-9,10-seco-cholesta-5,7,23-trien-24a-yne-1,3-diol.

27. A compound of claim 25, (7E,23E,24aE)- and (7E,23Z,24aE)-(1R,3R)-25-(1-hydroxy-cyclopentyl)-24a,24b-dihomo-19-nor-9,10-seco-cholesta-5,7,23,24a-tetraen-24a-yne-1,3-diol.

28. A compound of formula II:
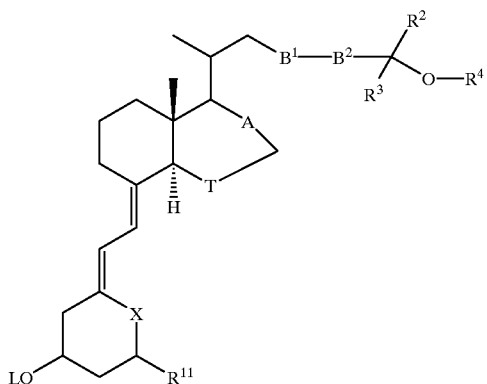
II
wherein $R^{11}$ is H, F or OL, $R^4$ is H or L', L and L' are silyl-protecting groups, and wherein
A is a single or double bond,
$B^1$ is CH=CH,
$B^2$ is CH=CH or C≡C,
T is $CH_2$ or $CH_2CH_2$,
X is —CH2— or >C=CH2,
$R^2$ and $R^3$ are each independently $C_{1-4}$-alkyl or $CF_3$, or
$C(R^2,R^3)$ is $C_{3-6}$-cycloalkyl.
* * * * *

UNITED STATES PATENT AND TRADEMARK OFFICE
CERTIFICATE OF CORRECTION

PATENT NO. : 5,994,569
DATED : Nov.30, 1999
INVENTOR(S) : Barbier, et al.

It is certified that error appears in the above-indentified patent and that said Letters Patent is hereby corrected as shown below:

IN THE CLAIMS

Claim 17, Column 28, lines 30-35, the formula reads

"  " The formula should read

---  --- .

Signed and Sealed this

Fourth Day of July, 2000

Attest:

Attesting Officer

Q. TODD DICKINSON

Director of Patents and Trademarks